US012344861B2

(12) United States Patent
Phan

(10) Patent No.: US 12,344,861 B2
(45) Date of Patent: Jul. 1, 2025

(54) METHOD OF ISOLATING MESENCHYMAL STEM CELLS FROM THE AMNIOTIC MEMBRANE OF THE UMBILICAL CORD, A MESENCHYMAL STEM CELL POPULATION ISOLATED FROM THE AMNIOTIC MEMBRANE OF THE UMBILICAL CORD AND A CELL CULTURE MEDIUM FOR ISOLATING MESENCHYMAL STEM CELLS FROM THE AMNIOTIC MEMBRANE OF THE UMBILICAL CORD

(71) Applicant: CELLRESEARCH CORPORATION PTE. LTD., Singapore (SG)

(72) Inventor: Toan Thang Phan, Singapore (SG)

(73) Assignee: CELLRESEARCH CORPORATION PTE. LTD., Singapore (SG)

( * ) Notice: Subject to any disclaimer, the term of this patent is extended or adjusted under 35 U.S.C. 154(b) by 0 days.

(21) Appl. No.: 18/387,192

(22) Filed: Nov. 6, 2023

(65) Prior Publication Data

US 2024/0141298 A1 May 2, 2024

Related U.S. Application Data

(60) Continuation of application No. 17/190,228, filed on Mar. 2, 2021, now Pat. No. 11,821,006, which is a division of application No. 15/725,913, filed on Oct. 5, 2017, now Pat. No. 10,988,736.

(60) Provisional application No. 62/404,582, filed on Oct. 5, 2016.

(51) Int. Cl.
*C12N 5/0775* (2010.01)
*A61K 35/28* (2015.01)
*A61K 35/50* (2015.01)

(52) U.S. Cl.
CPC ............ *C12N 5/0665* (2013.01); *A61K 35/28* (2013.01); *A61K 35/50* (2013.01); *C12N 5/0668* (2013.01); *C12N 2500/05* (2013.01); *C12N 2500/32* (2013.01); *C12N 2500/34* (2013.01); *C12N 2500/38* (2013.01); *C12N 2500/40* (2013.01); *C12N 2500/84* (2013.01); *C12N 2501/11* (2013.01); *C12N 2501/33* (2013.01); *C12N 2501/395* (2013.01); *C12N 2501/999* (2013.01); *C12N 2506/025* (2013.01)

(58) Field of Classification Search
None
See application file for complete search history.

(56) References Cited

U.S. PATENT DOCUMENTS

| 8,287,854 | B2 | 10/2012 | Phan |
| 9,085,755 | B2 | 7/2015 | Phan et al. |
| 9,737,568 | B2 | 8/2017 | Phan et al. |
| 10,988,736 | B2* | 4/2021 | Phan ............... A61K 35/28 |
| 11,821,006 | B2* | 11/2023 | Phan ............... C12N 5/0665 |
| 2006/0078993 | A1 | 4/2006 | Phan et al. |
| 2011/0151556 | A1* | 6/2011 | Kallis ............... A61K 35/44 435/309.1 |

FOREIGN PATENT DOCUMENTS

| CN | 101525594 A | 9/2009 |
| CN | 103266081 A | 8/2013 |
| CN | 103555655 A | 2/2014 |
| CN | 105420179 A | 3/2016 |
| CN | 105420184 A | 3/2016 |
| JP | 2008-509699 A | 4/2008 |
| JP | 2015-142559 A | 8/2015 |
| JP | 2016-510013 A | 4/2016 |
| KR | 10-2007-0053255 A | 5/2007 |
| WO | 2006019357 A1 | 2/2006 |
| WO | WO2007046775 A1 | 4/2007 |
| WO | 2014131877 A1 | 9/2014 |

OTHER PUBLICATIONS

Office Action issued in related Chinese Patent Application No. 201780061207.1 dated Nov. 22, 2023—incl Engl lang transl (23 pages total).
"DMEM:F12(1:1) medium" data sheet, Document #TS 12-719-3, 2011 (1 page).
"Dulbecco's modified eagle medium (DMEM)" data sheet, Document #TS 12-604-3, 2011 (2 pages).
"Ham's F12 Medium" data sheet, Document #TS 12-615-2, 2008 (1 page).
"Medium 171, Medium 171PRF, and MEGS", data sheet, 2009 (2 pages).
Arevalo et al., Cultivo de celulas madre mesenquimales a partir de sandre de cordon umbilical y medula osea. [Culture of Meneshymal Stem Cells from Umbilical Cord Blood and Bone Marrow]. Thesis, Pontifial Javeriana Univ Sci Facility, Bacteriology Dept, Bogota, DC 2007—incl Engl lang transl (290 pages total). accessed online at: https://www.javeriana.edu.co/biblos/tesis/ciencias/tesis 172. pdf.
Bianco et al., Mesenchymal Stem Cells: Revisiting History, Concepts, and Assays. Cell Stem Cell. Apr. 10, 2008;2 4):313-319.
Capelli et al., Clinical grade expansion of MSCs. Immunol Lett. Dec. 2015;168(2):222-227.
Caplan, Mesenchymal Stem Cells *. J Orthop Res. Sep. 1991;9(5):641-650.

(Continued)

*Primary Examiner* — Blaine Lankford
(74) *Attorney, Agent, or Firm* — Michael A. Whittaker

(57) ABSTRACT

The present invention relates to a method of cryopreserving a mesenchymal stem cell population, the method comprising: cultivating umbilical cord tissue in a culture medium comprising DMEM (Dulbecco's modified eagle medium), F12 (Ham's F12 Medium), M171 (Medium 171) and FBS (Fetal Bovine Serum) to provide outgrowth of mesenchymal stem cells present in the amniotic membrane of the umbilical cord; isolating the mesenchymal stem cell population by collecting the outgrown mesenchymal stem cells; and placing the isolated mesenchymal stem cell population in cryopreserved storage. The invention also relates to a cryopreserved mesenchymal stem population of the amniotic membrane of the umbilical cord.

4 Claims, 6 Drawing Sheets

(56) References Cited

OTHER PUBLICATIONS

Conconi et al., Phenotype and Differentiation Potential of Stromal Populations Obtained from Various Zones of Human Umbilical Cord: An Overview. The Open Tissue Engineering and Regenerative Medicine Journal. 2011;4:6-20.

Dimarino et al., Mesenchymal stem cells in tissue repair. Front Immunol. Sep. 4, 2013;4:201 (9 pages).

Do et al., Derivation of Hepatocytes from Human Umbilical Cord Lining Epithelial Stem Cells. Stem Cells: From Bench to Bedside 2nd Edition, Nov. 2010:323-337.

Dominici et al, Minimal criteria for defining multipotent mesenchymal stromal cells. The International Society for Cellular Therapy position statement Cytotherapy. 2006;8(4):315-317.

Garcia De Insausti, Isolation and characterization of the stem cells of the Amniotic Membrane. A new source for cell therapy and immunomodulation. Thesis, Univ of Murcia, School of Medicine 2012—incl Engl lang transl only (573 pages total).

Hanley et al., Efficient Manufacturing of Therapeutic Mesenchymal Stromal Cells Using the Quantum Cell Expansion System. Cytotherapy. Aug. 2014;16(8):1048-1058.

Jeschke et al., Umbilical Cord Lining Membrane and Wharton's Jelly-Derived Mesenchymal Stem Cells: the Similarities and Differences; The Open Tissue Engineering and Regenerative Medicine Journal, 2011;4:21-27.

Jin et al., Comparative Analysis of Human Mesenchymal Stem Cells from Bone Marrow, Adipose Tissue, and Umbilical Cord Blood as Sources of Cell Therapy. Int J Mol Sci. Sep. 3, 2013;14(9):17986-18001.

Kundrotas, Surface markers distinguishing mesenchymal stem cells from fibroblasts. Acta Medica Lituanica. 2012;19(2):75-79.

Lim and Phan, Epithelial and Mesenchymal Stem Cells from the Umbilical Cord Lining Membrane. Cell Transplant 2014;23(4-5):497-503.

Ng et al., Enhanced ex vivo expansion of adult mesenchymal stem cells by fetal mesenchymal stem cell ECM. Biomaterials. Apr. 2014;35(13):4046-4057.

Novokhatsky et al., The problem of cell contamination and new approaches to the control of continuous cell lines. Voprosy Virology. 1977;4:396-408—incl Eng lang summary (14 pages total).

Pirjali et al., Isolation and Characterization of Human Mesenchymal Stem Cells Derived from Human Umbilical Cord Wharton's Jelly and Amniotic Membrane. Int J Organ Transplant Med. 2013;4(3):111-116.

Salehinejad et al., Comparison of different methods for the isolation of mesenchymal stem cells from human umbilical cord Wharton's jelly. In Vitro Cell Dev Biol Anim. Feb. 2012;48(2):75-83.

Sensebe et al., Production of mesenchymal stromal/stem cells according to good manufacturing practices: a review. Stem Cell Res Ther. Jun. 7, 2013;4(3):66.

Smith et al., Standardizing Umbilical Cord Mesenchymal Stromal Cells for Translation to Clinical Use: Selection of GMP-Compliant Medium and a Simplified Isolation Method. Stem Cells Int. 2016;2016:6810980 (14 pages).

Stubbendorf et al., Immunological Properties of Extraembryonic Human Mesenchymal Stromal Cells Derived from Gestational Tissue. Stem Cells Dev. Oct. 1, 2013;22(19):2619-2629.

Subramanian et al., Comparative Characterization of Cells from the Various Compartments of the Human Umbilical Cord Shows that the Wharton's Jelly Compartment Provides the Best Source of Clinically Utilizable Mesenchymal Stem Cells. PLoS One. Jun. 1, 20150;10(6):e0127992 (25 pages).

Thermo Fisher Scientific—DE, Technical Resources—Media Formulations: Medium 171. XP055875556, Dec. 22, 2021. Retrieved from the Internet at: https://www.thermofisher.com/de/de/home/technical-resources/mediaformulation.283.html (3 pages).

Trukhan, The Culture Medium as a Key Factor of the Mammalian Cell Cultivation. International Journal of Applied and Basic Research. 2018; 12(1):165-172—incl Eng lang abstract only.

Turinetto et al., Senescence in Human Mesenchymal Stem Cells: Functional Changes and Implications in Stem Cell-Based Therapy. Int J Mol Sci. Jul. 19, 2016;17(7):1164 (18 pages).

Van Pham et al., Isolation and proliferation of umbilical cord tissue derived mesenchymal stem cells for clinical applications. Cell Tissue Bank. Jun. 2016;17(2):289-302.

Van Pham et al., Isolation of Breast Cancer Stem Cells by Single-Cell Sorting. Found in book: Biomedical Tissue Culture, Chapter 4: Isolation of Breast Cancer Stem Cells by Single-Cell Sorting. © 2012 (pp. 59-72).

Vechkanov et al., Fundamentals of Cell Engineering: Textbook. Tutorial.—Rostov-on-Don, 2012; 136 p.; pp. 15-17—incl Eng lang machine transl.

Vonk et al., Autologous, allogeneic, induced pluripotent stem cell or a combination stem cell therapy? Where are we headed in cartilage repair and why: a concise review. Stem Cell Res Ther. May 15, 2015;6:94.

Vu et al., Optimization of culture medium for the isolation and propagation of human breast cancer cells from primary tumour biopsies. Biomedical Research and Therapy. 2015;2(2):207-219.

Xi et al., Mesenchymal stem cells in tissue repairing and regeneration: Progress and future. Burns Trauma. Jun. 18, 2013;1(1):13-20.

Zhao et al., Large-scale expansion of Wharton's jelly-derived mesenchymal stem cells on gelatin microbeads, with retention of self-renewal and multipotency characteristics and the capacity for enhancing skin wound healing. Stem Cell Res Ther. Mar. 19, 2015;6:38 (16 pages).

Extended European Search Report and Written Opinion issued in EP 17858825 dated May 12, 2020 (9 pages).

International Search Report and Written Opinion issued in PCT/SG2017/050500 dated Jan. 31, 2018 (10 pages total).

Office Action issued by the Colombian Patent Office in Colombian Patent Application No. NC2019/0009515 dated Sep. 4, 2019—incl Engl lang translation (18 pages total).

Office Action issued by the Colombian Patent Office in Colombian Patent Application No. NC2019/0002569 dated Nov. 26, 2020—incl Engl lang transl only (need # of pages).

Office Action issued by the Colombian Patent Office in Colombian Patent Application No. NC2019/0002569 dated Jul. 2, 2021—incl Engl lang transl (need # of pages).

Office Action issued in related Russian Patent Application No. 2019100561/10 dated Feb. 15, 2021—incl Eng lang machine transl (14 pages total).

Extended Search Report issued in EP 17858825.7 dated Jan. 10, 2022 (6 pages).

Office Action issued by KIPO in Korean Patent Application No. 10-2019-7004328 dated Jan. 20, 2022—incl Engl Lang transl.

Office Action Issued by the JPO in Japanese Patent Application No. 2019-515832 dated Nov. 8, 2021—incl Engl lang transl (12 pages total).

Office Action Issued by the CNIPO in Chinese Patent Application No. 201780061207.1 dated Nov. 24, 2022—incl Engl lang transl (52 pages total).

* cited by examiner

*Fig. 1*

*PTT6 Medium ingredients list*

| Medium composition List | Company Name | Catalogue Number |
|---|---|---|
| Basic media | | |
| DMEM (also referred to herein as PTT6-basal medium) | Lonza | 12-604F |
| DMEM/F12 | Lonza | 12-719F |
| M171 | Life technologies | M171500 |
| Serum | | |
| Fetal Bovine Serum | GE Healthcare | A15-151 |
| Antibiotic | | |
| Penicillin-Streptomycin-Amphotericin B | Lonza | 17-745E |
| Supplements | | |
| Adenine (optional) | Sigma | A8626-25G |
| Hydrocortisone (optional) | Sigma | H-0888 |
| Epidermal Growth Factor | Millipore | GF-144 |
| T3 (3,3',5-Triiodo-L-thyronine sodium salt) (optional) | Sigma | 200-223-5 |
| Recombinant Human Insulin AOF | Life Technologies | A11382IJ |

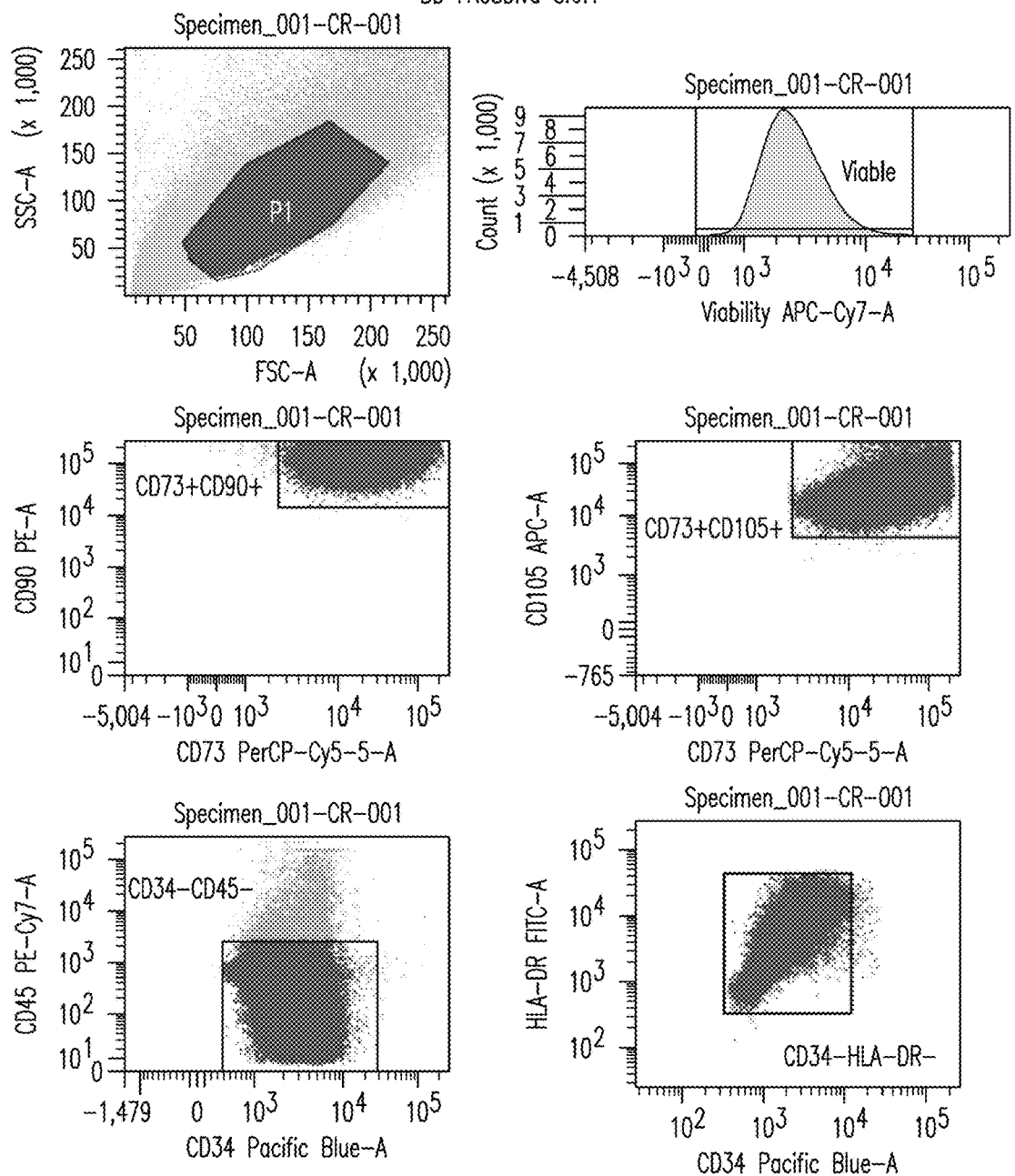

METHOD OF ISOLATING MESENCHYMAL STEM CELLS FROM THE AMNIOTIC MEMBRANE OF THE UMBILICAL CORD, A MESENCHYMAL STEM CELL POPULATION ISOLATED FROM THE AMNIOTIC MEMBRANE OF THE UMBILICAL CORD AND A CELL CULTURE MEDIUM FOR ISOLATING MESENCHYMAL STEM CELLS FROM THE AMNIOTIC MEMBRANE OF THE UMBILICAL CORD

CROSS-REFERENCE TO RELATED APPLICATIONS

The present application is a continuation application of U.S. patent application Ser. No. 17/190,228, filed Mar. 2, 2021, now U.S. Pat. No. 11,821,006, which is a divisional application of U.S. patent application Ser. No. 15/725,913 filed Oct. 5, 2017, now U.S. Pat. No. 10,988,736, which claims the benefit of priority of U.S. Provisional Application No. 62/404,582, filed Oct. 5, 2016, the contents of each of which are hereby incorporated by reference it their entirety for all purposes.

FIELD OF THE INVENTION

The present invention relates to a method of isolating mesenchymal stem cells (or such a stem cell population from the amniotic membrane of umbilical cord, as well as a mesenchymal stem cell population isolated from the amniotic membrane of the umbilical cord. The invention is also directed to a cell culture medium for isolating mesenchymal stem cells from the amniotic membrane of the umbilical cord. The invention is also directed to a pharmaceutical composition and uses of the isolated mesenchymal stem cell population. The invention is also directed to methods of treating a disease or disorder comprising administering a mesenchymal stem cell population or a pharmaceutical composition containing such a mesenchymal stem cell population of the invention to a subject in need thereof.

BACKGROUND OF THE INVENTION

Mesenchymal stem cells isolated from the amniotic membrane of the umbilical cord have been first reported in US patent application 2006/0078993 (leading to granted U.S. Pat. Nos. 9,085,755 and 9,737,568) and the corresponding International patent application WO2006/019357. Since then, the umbilical cord tissue has gained attention as a source of multipotent cells; due to its widespread availability, the umbilical cord and in particular stem cells isolated from the amniotic membrane of the umbilical cord (also referred to as "cord lining stem cells") have been considered as an excellent alternative source of cells for regenerative medicine. See, Jeschke et al. Umbilical Cord Lining Membrane and Wharton's Jelly-Derived Mesenchymal Stem Cells: the Similarities and Differences; The Open Tissue Engineering and Regenerative Medicine Journal, 2011, 4, 21-27.

A subsequent study compared the phenotype, proliferation rate, migration, immunogenicity, and immunomodulatory capabilities of human mesenchymal stem cells (MSCs) derived from the amniotic membrane of the umbilical cord (umbilical cord lining (CL-MSCs), umbilical cord blood (CB-MSCs), placenta (P-MSCs), and Wharton's jelly (WJ-MSCs) (Stubbendorf et al, Immunological Properties of Extraembryonic Human Mesenchymal Stromal Cells Derived from Gestational Tissue, STEM CELLS AND DEVELOPMENT Volume 22, Number 19, 2013, 2619-2629. Stubbendorf et al concluded that extraembryonic gestational tissue-derived MSC populations show a varied potential to evade immune responses as well as exert immunomodulatory effects. The authors also found that CL-MSCs showed the most promising potential for a cell-based therapy, as the cells showed low immunogenicity, but they also showed enhanced proliferative and migratory potential so that future research should concentrate on the best disease models in which CL-MSCs could be administered.

While mesenchymal stem cells of the amniotic membrane can easily be obtained using the protocol as described in US patent application 2006/0078993 and International patent application WO2006/019357, it would be of advantage for clinical trials with these cord lining MSC to have at hand a method that allows to isolate a population of these cord lining MSC's that is highly homogenous and can thus be used for clinical trials.

Accordingly, it is an object of the invention to provide a method of isolating a population of mesenchymal stem cells from the amniotic membrane of umbilical cord that meets this need. It is thus also an object of the invention to provide a highly homogenous population of mesenchymal stem cells isolated from the amniotic membrane of the umbilical cord.

SUMMARY OF THE INVENTION

This object is accomplished by the methods, the mesenchymal stem population, the respective pharmaceutical composition and cell culture medium having the features of the independent claims.

In a first aspect, the invention provides a method of isolating a mesenchymal stem cell population from the amniotic membrane of the umbilical cord, the method comprising cultivating umbilical cord tissue in a culture medium comprising DMEM (Dulbecco's modified eagle medium), F12 (Ham's F12 Medium), M171 (Medium 171) and FBS (Fetal Bovine Serum).

In a second aspect, the invention provides an isolated mesenchymal stem population of the amniotic membrane of the umbilical cord, wherein at least about 90% or more cells of the stem cell population express each of the following markers: CD73, CD90 and CD105. Preferably, the isolated mesenchymal stem population lack expression of the following markers: CD34, CD45 and HLA-DR. In embodiments of this second aspect, at least about 91% or more, about 92% or more, about 92% or more, about 93% or more, about 94% or more, about 95% or more, about 96% or more, about 97% or more, about 98% or more about 99% or more cells of the isolated mesenchymal stem cell population express each of CD73, CD90 and CD105. In addition, in these embodiments of the second aspect, at least about 91% or more, about 92% or more, about 92% or more, about 93% or more, about 94% or more, about 95% or more, about 96% or more, about 97% or more, about 98% or more about 99% or more cells of the isolated mesenchymal stem cell population preferably lack expression of the markers CD34, CD45 and HLA-DR. The mesenchymal stem cell population may be obtained by a method of isolating a mesenchymal stem cell population of the first aspect.

In a third aspect, the invention provides a pharmaceutical composition containing a mammalian cell of (the second aspect of) the invention.

In a fourth aspect, the invention provides a method of making a culture medium for isolating the method comprising mixing to obtain a final volume of 500 ml culture medium:
  i. 250 ml of DMEM
  ii. 118 ml M171
  iii. 118 ml DMEM/F12
  iv. 12.5 ml Fetal Bovine Serum (FBS) to obtain a final concentration of 2.5% (v/v).

In a fifth aspect, the invention provides a cell culture medium obtainable by the method of the fourth aspect.

In a sixth aspect, the invention provides a method of isolating mesenchymal stem cells from the amniotic membrane of the umbilical cord, comprising cultivating amniotic membrane tissue in the culture medium prepared by the method of the fourth aspect.

In a seventh aspect, the invention provides a cell culture medium comprising:
  DMEM in the final concentration of about 55 to 65% (v/v),
  F12 in a final concentration of about 5 to 15% (v/v),
  M171 in a final concentration of about 15 to 30% (v/v) and
  FBS in a final concentration of about 1 to 8% (v/v).

In an eight aspect, the invention provides the use of a cell culture medium of the seventh aspect for the isolation of mesenchymal stem cells from the amniotic membrane of umbilical cord.

In a ninth aspect, the invention provides the use of a cell culture medium of the seventh aspect for the cultivation of mesenchymal stem cells from the amniotic membrane of umbilical cord.

BRIEF DESCRIPTION OF THE DRAWINGS

The invention will be better understood with reference to the detailed description when considered in conjunction with the non-limiting examples and the drawings, in which:

FIG. 1 shows the list of ingredients, including their commercial supplier and the catalogue number that have been used in the Experimental Section for the making of the medium PTT-6.

FIG. 2a shows the percentage of isolated mesenchymal cord lining stem cells expressing stem cell markers CD73, CD90 and CD105 after isolation from umbilical cord tissue and cultivation in DMEM/10% FBS.

FIG. 2b shows the percentage of isolated mesenchymal cord lining stem cells expressing stem cell markers CD73, CD90 and CD105 after isolation from umbilical cord tissue and cultivation in PTT-4.

FIG. 2c shows the percentage of isolated mesenchymal cord lining stem cells expressing stem cell markers CD73, CD90 and CD105 after isolation from umbilical cord tissue and cultivation in PTT-6.

FIGS. 3a-3b show the results of flow cytometry experiments in which mesenchymal stem cells isolated from the umbilical cord have been analysed for their expression of stem cells markers (CD73, CD90 and CD105, CD34, CD45 and HLA-DR (Human Leukocyte Antigen—antigen D Related) that are used for defining the suitability of multipotent human mesenchymal stem cells for cellular therapy and compared to the expression of these markers by bone marrow mesenchymal stem cells. For this experiment, the mesenchymal stem cells of the aminotic membrane of the umbilical cord were isolated from umbilical cord tissue by cultivation of the umbilical cord tissue in the culture medium of the present invention PPT-6 while the bone marrow mesenchymal stem cells were isolated from human bone marrow using a standard protocol.

FIG. 3a shows the percentage of isolated mesenchymal cord lining stem cells that express the stem cell markers CD73, CD90 and CD105 and lack expression of CD34, CD45 and HLA-DR after isolation from umbilical cord tissue and cultivation in PTT-6 medium.

FIG. 3b shows the percentage of isolated bone marrow mesenchymal stem cells that express CD73, CD90 and CD105 and lack expression of CD34, CD45 and HLA-DR.

DETAILED DESCRIPTION OF THE INVENTION

Figure 2A:
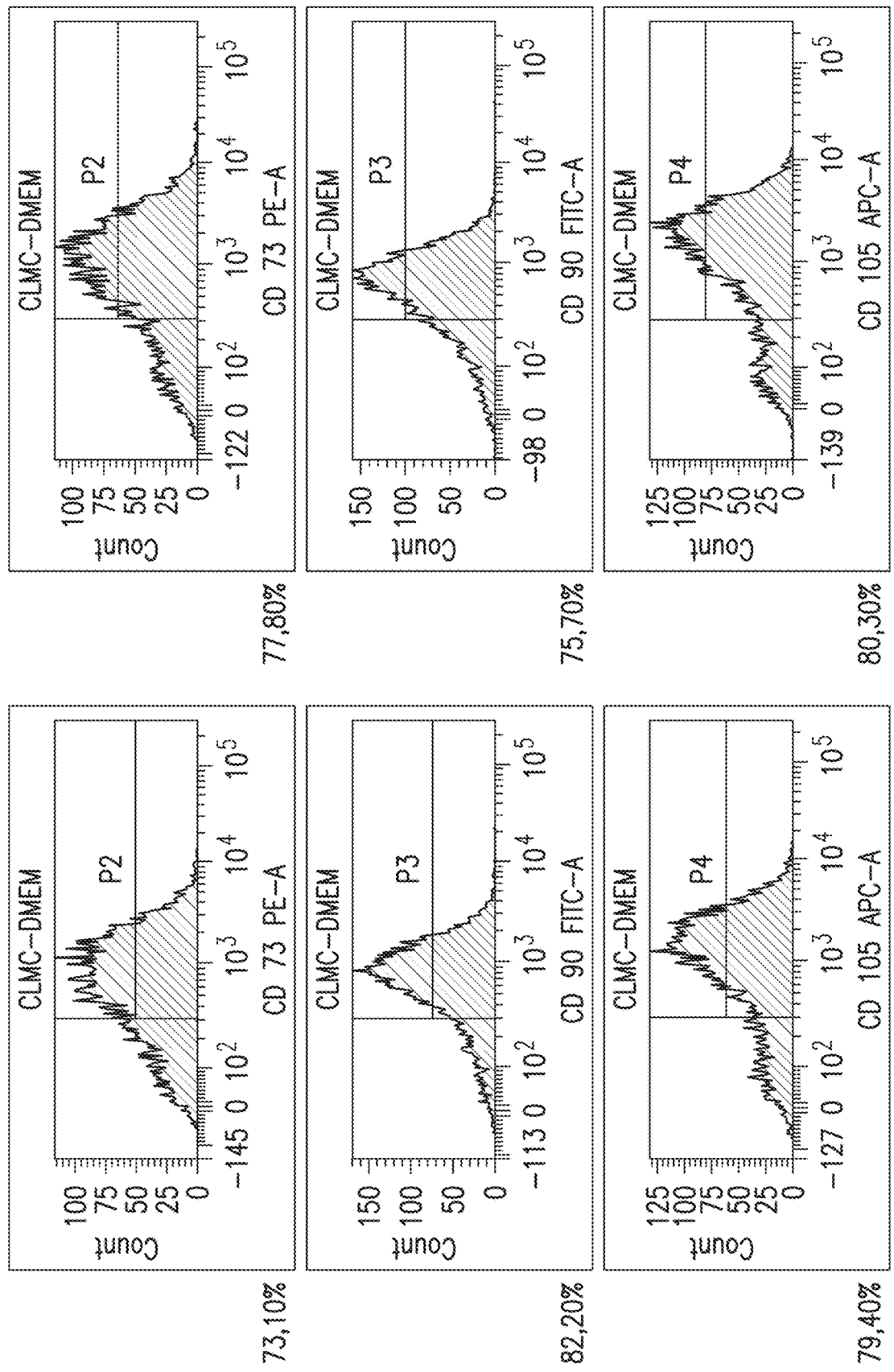
FIGS. 2a-2c show the results of flow cytometry experiments in which mesenchymal stem cells isolated from the umbilical cord have been analysed for the expression of the mesenchymal stem cell markers CD73, CD90 and CD105. For these experiments, mesenchymal stem cells were isolated from umbilical cord tissue by cultivation of the umbilical cord tissue in three different cultivation media, followed by subculturing of the mesenchymal stem cells in the respective medium. The three following culture media were used in these experiments: a) 90% (v/v/DMEM supplemented with 10% FBS (v/v), b) the culture medium PTT-4 described in US patent application 2006/0078993 and the corresponding International patent application WO2006/019357 that consist of 90% (v/v) CMRL1066, and 10% (v/v) FBS (see paragraph of WO2006/019357 and c) the culture medium of the present invention PPT-6 the composition of which is described herein. In this flow cytometry analysis, two different samples of the cord lining mesenchymal stem cell (CLMC) population were analysed for each of the three used culture media. The results are shown in FIG. 2a to FIG. 2c.

As explained above, in a first aspect the invention is directed to a method of isolating a mesenchymal stem cell population from the amniotic membrane of the umbilical cord, the method comprising cultivating umbilical cord tissue in a culture medium comprising DMEM (Dulbecco's modified eagle medium), F12 (Ham's F12 Medium), M171 (Medium 171) and FBS (Fetal Bovine Serum). It has been surprisingly found in the present application that using such a medium provides for the isolation of a mesenchymal stem cell population from the amniotic membrane of the umbilical cord of which more than 90%, or even 99% or more of the cells are positive for the three mesenchymal stem cell markers CD73, CD90 and while at the same these stem cells lack expression of CD34, CD45 and HLA-DR (see the Experimental Section), meaning 99% or even more cells of this population express the stem cell markers CD73, CD90 and CD105 while not expressing the markers CD34, CD45 and HLA-DR. Such an extremely homogenous and well defined cell population is the ideal candidate for clinical trials and cell based therapies since, they for example, fully meet the criteria generally accepted for human mesenchymal stem cells to be used for cellular therapy as defined, for example, by Dominici et al, "Minimal criteria for defining multipotent mesenchymal stromal cells. The International Society for Cellular Therapy position statement", Cytotherapy (2006) Vol. 8, No. 4, 315-317, Sensebe et al., "Production of mesenchymal stromal/stem cells according to good manufacturing practices: a, review", Stem Cell Research & Therapy 2013, 4:66), Vonk et al., Stem Cell Research & Therapy (2015) 6:94, or Kundrotas Acta Medica Lituanica. 2012. Vol. 19. No. 2. P. 75-79. Also, using a bioreactor such as a Quantum Cell Expansion System, it is possible to obtain high numbers of mesenchymal stem cells such as 300 to 700 million mesenchymal stem cells per run (see also the Experimental Section). Thus, the present invention allows to provide the amounts of stem cells that are needed for therapeutic applications such as their use in wound healing in a cost efficient manner. In addition, all components used for making the culture medium of the present invention are commercially available in GMP quality. Accordingly, the present invention opens the route to the GMP production of this highly homogenous mesenchymal stem cell population from the amniotic membrane of the umbilical cord.

In this context, it is noted that the culture medium of the present invention allows the isolation of a mesenchymal stem cell population (also referred hereas as "mesenchymal stem cells") from the amniotic membrane under conditions that allow cell proliferation of the mesenchymal stem/progenitor cells without differentiation of the mesenchymal stem/progenitor cells. Thus, after isolation of the mesenchymal stem cells from the amniotic membrane as described herein the isolated mesenchymal stem/progenitor cell population has the capacity to differentiate into multiple cell types as described in US patent application 2006/0078993, U.S. Pat. No. 9,085,755, International patent application WO2006/019357, U.S. Pat. No. 8,287,854 or WO2007/046775, for instance. As described in US patent application 2006/0078993, for example, the mesenchymal stem cells of the amniotic membrane of the umbilical cord have a spindle shape, express the following genes: POU5f1, Bmi-1, leukemia inhibitory factor (LIF), and secrete Activin A and Follistatin. The mesenchymal stem cells isolated in the present invention can, for example, be differentiated into any type of mesenchymal cell such as, but not limited to, adipocyte, skin fibroblasts, chondrocytes, osteoblasts, tenocytes, ligament fibroblasts, cardiomyocytes, smooth muscle cells, skeletal muscle cells, adipocytes, mucin producing cells, cells derived from endocrine glands such as insulin producing cells (for example, β-islet cells) or neurectodermal cells. The stem cells isolated in the present invention can be differentiated in vitro in order to subsequently use the differentiated cell for medical purposes. An illustrative example of such an approach is the differentiation of the mesenchymal stem cells into insulin producing β-islet cells which can then be administered, for example by implantation, to a patient that suffers from an insulin deficiency such as diabetes mellitus (cf. also WO2007/046775 in this respect). Alternatively, the mesenchymal stem cells of the invention can be used in their undifferentiated state for cell based therapy, for example, for wound healing purposes such as treatment of burns or chronic diabetic wounds. In these therapeutic applications the mesenchymal stem cells of the invention can either serve to promote wound healing by interacting with the surrounding diseased tissue or can also differentiate into a respective skin cell (cf., again WO2007/046775, for example).

In this context, it is noted that the mesenchymal stem cell population described herein can be isolated and cultivated (i.e. are derived) from any umbilical cord tissue as long as the umbilical cord tissue contains the amniotic membrane (which is also referred to as "cord lining"). Accordingly, the mesenchymal stem cell population can be isolated from (pieces of) the entire umbilical cord as described in the Experimental section of the present application. This umbilical cord tissue may thus contain, in addition to the amniotic membrane, any other tissue/component of the umbilical cord. As shown, for example, in FIG. 16 of US patent application 2006/0078993 or International patent application WO2006/019357, the amniotic membrane of the umbilical cord is the outmost part of the umbilical cord, covering the cord. In addition, the umbilical cord contains one vein (which carries oxygenated, nutrient-rich blood to the fetus) and two arteries (which carry deoxygenated, nutrient-depleted blood away from the fetus). For protection and mechanical support these three blood vessels are embedded in the Wharton's jelly, a gelatinous substance made largely from mucopolysaccharides. Accordingly, the umbilical cord tissue used in the present invention can also comprise this one vein, the two arteries and the Wharton's jelly. The use of such an entire (intact) section of the umbilical cord has the advantage that the amniotic membrane does not need to be separated from the other components of the umbilical cord. This reduces the isolation steps and thus makes the method of the present invention, simpler, faster, less error prone and more economical—which are all important aspects for the GMP production that is necessary for therapeutic application of the mesenchymal stem cells. The isolation of the mesenchymal stem cells can thus start by tissue explant, which may be followed by subsequent subculturing (cultivation) of the isolated mesenchymal stem cells if greater amounts of the mesenchymal stem cells are desired, for example, for use in clinical trials. Alternatively, it is also possible to first separate the amniotic membrane from the other components of the umbilical cord and isolate the mesenchymal cord lining stem cells from the amniotic membrane by cultivation of the amniotic membrane in a culture medium of the present invention. This cultivation can also be carried out by tissue explant, optionally followed by subculturing of the isolated mesenchymal stem cells. In this context, the term "tissue explant" or "tissue explant method" is used in its regular meaning in the art to refer a method in which a tissue, once being harvested, or a piece of the tissue is being placed in a cell culture dish containing culture (growth) medium and by which over time, the stem cells migrate out of the tissue onto the surface of the dish. These primary stem cells can then be further expanded and transferred into fresh dishes through micropropagation (subculturing) as also described here. In this context, it is noted that in terms of production of the cells for therapeutic purposes, in the first step of isolating the amniotic membrane mesenchymal stem cells from the umbilical cord, a master cell bank of the isolated mesenchymal stem cells is obtained, while the subsequent subculturing a working cell bank can be obtained. If a mesenchymal stem cell population of the invention (in particular a population of the mesenchymal stem cells of which at least about 98% or 99% or express each of the markers CD73, CD90 and CD105 and lack expression of each of the markers: CD34, CD45 and HLA-DR) is used for clinical trials or as an approved therapeutic, a cell population of the working cell bank will be typically used for this purpose. Both the stem cell population of the isolation step (which may make up the master cell bank) and the stem cell population of the subculturing step (which may make up the working cell bank) can, for example, be stored in cryo-preserved form.

As mentioned above, the present method of isolating mesenchymal stem cells from the amniotic membrane of umbilical cord has the advantage that all components used in the culture medium of the invention are available in GMP quality and thus provide the possibility to isolate the mesenchymal stem cells under GMP conditions for subsequent therapeutic administration.

By "DMEM" is meant Dulbecco's modified eagle medium which was developed in 1969 and is a modification of basal medium eagle (BME) (cf. TS-12-604-3, Lonza Walkersville, Inc., August 2011). The original DMEM formula contains 1000 mg/L of glucose and was first reported for culturing embryonic mouse cells. DMEM has since then become a standard medium for cell culture that is commercially available from various sources such as ThermoFisher Scientific (catalogue number 11965-084), Sigma Aldrich (catalogue number D5546) or Lonza, to new only a few suppliers. Thus, any commercially available DMEM can be used in the present invention. In preferred embodiments, the DMEM used herein is the DMEM medium available from Lonza under catalog number 12-604F. This medium is DMEM supplemented with 4.5 g/L glucose and L-glutamine). In another preferred embodiment the DMEM used herein is the DMEM medium of Sigma Aldrich catalogue number D5546 that contains 1000 mg/L glucose, and sodium bicarbonate but is without L-glutamine.

By "F12" medium is meant Ham's F12 medium. This medium is also a standard cell culture medium and is a nutrient mixture initially designed to cultivate a wide variety of mammalian and hybridoma cells when used with serum in combination with hormones and transferrin (cf. TS-12-615-2, Lonza Walkersville, Inc., November. Any commercially available Ham's F12 medium (for example, from ThermoFisher Scientific (catalogue number 11765-054), Sigma Aldrich (catalogue number N4888) or Lonza, to new only a few suppliers) can be used in the present invention. In preferred embodiments, Ham's F12 medium from Lonza is used.

By "DMEM/F12" or "DMEM:F12" is meant a 1:1 mixture of DMEM with Ham's F12 culture medium (cf. TS-12-719-3, Lonza Walkersville, Inc., August 2011. Also DMEM/F12 (1:1) medium is a widely used basal medium for supporting the growth of many different mammalian cells and is commercially available from various supplier such as ThermoFisher Scientific (catalogue number 11330057), Sigma Aldrich (catalogue number D6421) or Lonza. Any commercially available DMEM:F12 medium can be used in the present invention. In preferred embodiments, the DMEM:F12 medium used herein is the DMEM/F12 (1:1) medium available from Lonza under catalog number 12-719F (which is DMEM: F12 with L-glutamine, 15 mM HEPES, and 3.151 g/L glucose).

By "M171" is meant culture medium 171, which has been developed as basal medium for the culture of for the growth of normal human mammary epithelial cells (cf. MAN0001585, Life Technologies Corporation, May 30, 2009). Also this basal medium is widely used and is commercially available from supplier such as ThermoFisher Scientific or Life Technologies Corporation (catalogue number M171500), for example. Any commercially available M171 medium can be used in the present invention. In preferred embodiments, the M171 medium used herein is the M171 medium available from Life Technologies Corporation under catalogue number M171500.

By "FBS" is meant fetal bovine serum (that is also referred to as "fetal calf serum"), i.e. the blood fraction that remains after the natural coagulation of blood, followed by centrifugation to remove any remaining red blood cells. Fetal bovine serum is the most widely used serum-supplement for in vitro cell culture of eukaryotic cells because it has a very low level of antibodies and contains more growth factors, allowing for versatility in many different cell culture applications. The FBS is preferably obtained from a member of the International Serum Industry Association (ISIA) whose primary focus is the safety and safe use of serum and animal derived products through proper origin traceability, truth in labeling, and appropriate standardization and oversight. Suppliers of FBS that are ISIA members include Abattoir Basics Company, Animal Technologies Inc., Biomin Biotechnologia LTDA, GE Healthcare, Gibco by Thermo Fisher Scientific and Life Science Production, to mention only a few. In currently preferred embodiments, the FBS is obtained from GE Healthcare under catalogue number A15-151.

Turning now to the culture medium of the present invention, the culture medium may comprise for the isolation or cultivation of the mesenchymal cord lining stem cells DMEM in a final concentration of about 55 to 65% (v/v), F12 in a final concentration of about 5 to 15% (v/v), M171 in a final concentration of about 15 to 30% (v/v) and FBS in a final concentration of about 1 to 8% (v/v). The value of "% (v/v)" as used herein refers to the volume of the individual component relative to the final volume of the culture medium. This means, if DMEM is, for example, present in the culture medium a final concentration of about 55 to 65% (v/v), 1 liter of culture medium contains about 550 to 650 ml DMEM.

In other embodiments, the culture medium may comprise DMEM in a final concentration of about 57.5 to 62.5% (v/v), F12 in a final concentration of about 7.5 to 12.5% (v/v), M171 in a final concentration of about 17.5 to 25.0% (v/v) and FBS in a final concentration of about 1.75 to 3.5% (v/v). In further embodiments, the culture medium may comprise DMEM in a final concentration of about 61.8% (v/v), F12 in a final concentration of about 11.8% (v/v), M171 in a final concentration of about 23.6% (v/v) and FBS in a final concentration of about 2.5% (v/v).

In addition to the above-mentioned components, the culture medium may comprise supplements that are advantages for cultivation of the mesenchymal cord lining stem cells. The culture medium of the present invention may, for example, comprises Epidermal Growth Factor (EGF). If present, EGF may be present in the culture medium in a final concentration of about 1 ng/ml to about 20 ng/ml. In some of these embodiments, the culture medium may comprise EGF in a final concentration of about 10 ng/ml.

The culture medium of the present invention may also comprises insulin. If present, insulin may be present in a final concentration of about 1 µg/ml to 10 µg/ml. In some of these embodiments, the culture medium may comprise Insulin in a final concentration of about 5 µg/ml.

The culture medium may further comprises at least one of the following supplements: adenine, hydrocortisone, and 3,3',5-Triiodo-L-thyronine sodium salt (T3). In such embodiments, the culture medium may comprise all three of adenine, hydrocortisone, and 3,3',5-Triiodo-L-thyronine sodium salt (T3). In these embodiments, the culture medium may comprises may comprise adenine in a final concentration of about 0.05 to about 0.1 µg/ml adenine, hydrocortisone in a final concentration of about 1 to about 10 µg/ml hydrocortisone and/or 3,3',5-Triiodo-L-thyronine sodium salt (T3) in a final concentration of about 0.5 to about 5 ng/ml.

In the method of the invention, the umbilical cord tissue may be cultured till a suitable number of (primary) mesenchymal cord lining stem cells have outgrown from the tissue. In typical embodiments, the umbilical cord tissue is cultivated until cell outgrowth of the mesenchymal stem cells of the amniotic membrane reaches about 70 to about 80% confluency. It is noted here that the term "confluency" or "confluence" is used in its regular meaning in the art of cell culture and is meant as an estimate/indicator of the number of adherent cells in a culture dish or a flask, referring to the proportion of the surface which is covered by cells. For example, 50 percent confluence means roughly half of the surface is covered and there is still room for cells to grow. 100 percent confluence means the surface is completely covered by the cells, and no more room is left for the cells to grow as a monolayer.

Once a suitable number of primary cells (mesenchymal cord lining stem cells) have been obtained from the cord lining tissue by tissue explant, the mesenchymal stem cells are removed from the cultivation container used for the cultivation. By so doing, a master cell bank containing the (primary) isolated mesenchymal stem cells of the amniotic membrane can be obtained. Typically, since mesenchymal stem cells are adherent cells, removing is carried out using standard enzymatic treatment. For example, the enzymatic treatment may comprise trypsination as described in International US patent application 2006/0078993, International patent application WO2006/019357 or International patent application WO2007/046775, meaning outgrowing cells can be harvested by trypsinization (0.125% trypsin/0.05% EDTA) for further expansion. If the harvested mesenchymal stem cells are, for example, used for generating a master cell bank, the cells can also be cryo-preserved and stored for further use as explained herein below.

Once being harvested, the mesenchymal stem cells can be transferred to a cultivation container for subculturing. The subculturing can also be started from frozen primary cells, i.e. from the master cell bank. For subculturing any suitable amount of cells can be seeded in a cultivation container such as cell culture plate. The mesenchymal cells can, for this purpose, be suspended in a suitable medium (most conveniently, the culture medium of the present invention) for subculturing at a concentration of, for example, about 0.5× $10^6$ cells/ml to about 5.0×$10^6$ cells/ml. In one embodiment the cells are suspended for subcultivation at a concentration of about 1.0×$10^6$ cells/ml. The subculturing can be carried by cultivation either in simple culture flasks but also, for example, in a multilayer system such as CellStacks (Corning, Corning, NY, USA) or Cellfactory (Nunc, part of Thermo Fisher Scientific Inc., Waltham, MA, USA) that can be stacked in incubators. Alternatively, the subculturing can also be carried out in a closed self-contained system such as a bioreactor. Different designs of bioreactors are known to the person skilled in the art, for example, parallel-plate, hollow-fiber, or micro-fluidic bioreactors. See, for example, Sensebe et al. "Production of mesenchymal stromal/stem cells according to good manufacturing practices: a review", supra. An illustrative example of a commercially hollow-fiber bioreactor is the Quantum® Cell Expansion System (Terumo BCT, Inc). that has, for example, been used for the expansion of bone marrow mesenchymal stem cells for clinical trials (cf., Hanley et al, Efficient Manufacturing of Therapeutic Mesenchymal Stromal Cells Using the Quantum Cell Expansion System, Cytotherapy. 2014 August; 16(8): 1048-1058). Another example of a commercially available bioreactors that can be used for the subculturing of the mesenchymal stem cell population of the present invention is the Xuri Cell Expansion System available from GE Heathcare. The cultivation of the mesenchymal stem cell population in an automated system such as the Quantum® Cell Expansion System is of particular benefit if a working cell bank for therapeutic application is to be produced under GMP conditions and a high number of cells is wanted.

The subculturing of the mesenchymal cord ling stem cells of the invention takes place in in a culture medium of the present invention. Accordingly, the culture medium of the present invention can be used both for the isolation of the mesenchymal stem cells from the amniotic membrane and the subsequent cultivation of the isolated primacy cells by subcultivation. Also for the subcultivation, the mesenchymal stem cells can be cultured till a suitable amount of cells have grown. In illustrative embodiments the mesenchymal stem cells are subcultured till the mesenchymal stem cells reach about 70 to about 80% confluency.

The isolation/cultivation of the population of mesenchymal cord lining stem cells can be carried out under standard condition for the cultivation of mammalian cells. Typically, the method of the invention of isolating the population of the mesenchymal cord lining stem cells is typically carried out at conditions (temperature, atmosphere) that are normally used for cultivation of cells of the species of which the cells are derived. For example, human umbilical cord tissue and the mesenchymal cord lining stem cells, respectively, are usually cultivated at 37° C. in air atmosphere with 5% $CO_2$. In this context, it is noted that the in present invention the mesenchymal cells may be derived of any mammalian species, such as mouse, rat, guinea pig, rabbit, goat, horse, dog, cat, sheep, monkey or human, with mesenchymal stem cells of human origin being preferred in one embodiment.

Once a desired/suitable number of mesenchymal cord lining stem cells have been obtained from the subculture, the mesenchymal stem cells are harvested by removing them from the cultivation container used for the subcultivation. The harvesting of the mesenchymal stem cells is typically again carried out by enzymatic treatment, including comprises trypsination of the cells. The isolated mesenchymal stem cells are subsequently collected and are either be directedly used or preserved for further use. Typically, preserving is carried out by cryo-preservation. The term "cryo-preservation" is used herein in its regular meaning to describe a process where the mesenchymal stem cells are preserved by cooling to low sub-zero temperatures, such as (typically) −80° C. or −196° C. (the boiling point of liquid nitrogen). Cryo-preservation can be carried out as known to the person skilled in the art and can include the use of cryo-protectors such as dimethylsulfoxide (DMSO) or glycerol, which slow down the formation of ice-crystals in the cells of the umbilical cord.

The isolated population of the mesenchymal cord lining stem cells that is obtained by the isolation method of the present invention is highly defined and homogenous. In typical embodiments of the method at least about 90% or more, about 91% or more, about 92% or more, about 92% or more, about 93% or more, about 94% or more, about 95% or more, about 96% or more, about 97% or more, about 98% or more about 99% or more of the isolated mesenchymal stem cells express the following markers: CD73, CD90 and CD105. In addition, in these embodiments at least about 90% or more, about 91% or more, about 92% or more, about 92% or more, about 93% or more, about 94% or more, about 95% or more, about 96% or more, about 97% or more, about 98% or more about 99% or more of the isolated mesenchymal stem cells may lack expression of the lack expression of the following markers: CD34, CD45 and HLA-DR. In particular embodiments, about 97% or more, about 98% or more, or about 99% or more of the isolated mesenchymal stem cell population express CD73, CD90 and CD105 while lacking expression of CD34, CD45 and HLA-DR.

Thus, in line with the above disclosure the present invention is also directed to a mesenchymal stem population isolated from the amniotic membrane of the umbilical cord, wherein at least about 90% or more cells of the stem cell population express each of the following markers: CD73, CD90 and CD105. In preferred embodiments at least about 91% or more, about 92% or more, about 92% or more, about 93% or more, about 94% or more, about 95% or more, about 96% or more, about 97% or more, about 98% or more about 99% or more cells of the isolated mesenchymal stem cell population are CD73+, CD90+ and CD105+, meaning that this percentage of the isolate cell population express each of CD73, CD90 and CD105 (cf. the Experimental Section of the present application). In addition, at least about 90% or more, about 91% or more, about 92% or more, about 92% or more, about 93% or more, about 94% or more, about 95% or more, about 96% or more, about 97% or more, about 98% or more about 99% or more of the isolated mesenchymal stem cells may lack expression of the lack expression of the following markers. In particular embodiments about 97% or more, about 98% or more, or about 99% or more of the isolated mesenchymal stem cell population express CD73, CD90 and CD105 while lacking expressing of CD34, CD45 and HLA-DR. Such a highly homogenous population of mesenchymal stem cells derived from the amniotic membrane of the umbilical cord has been reported here for the first time and meets the criteria for mesenchymal stem cells to be used for cellular therapy (also cf. the Experimental Section and, for example, Sensebe et al. "Production of mesenchymal stromal/stem cells according to good manufacturing practices: a review", supra). It is noted in this context that this mesenchymal stem cell population can be obtained by either the isolating method of the present invention but also by a different method such as cell sorting, if wanted.

In line with the above, the present invention is also directed to a pharmaceutical composition comprising a mesenchymal stem population isolated from the amniotic membrane of the umbilical cord, wherein at least about 90% or more cells of the stem cell population express each of the following markers: CD73, CD90 and CD105 and optionally, lack expression of CD34, CD45 and HLA-DR. The pharmaceutical composition may comprise any pharmaceutically acceptable excipient and may be formulated for any desired pharmaceutical way of administration. The pharmaceutical composition may, for example, be adapted for systemic or topical application.

In a further aspect the invention is directed to a method of making a culture medium for isolating the method comprising, mixing to obtain a final volume of 500 ml culture medium:
  i. 250 ml of DMEM
  ii. 118 ml M171
  iii. 118 ml DMEM/F12
  iv. 12.5 ml Fetal Bovine Serum (FBS) to reach a final concentration of 2.5% (v/v).

As explained above, DMEM/F12 medium is a 1:1 mixture of DMEM and Ham's F12 medium. Thus, 118 ml DMEM/F12 medium contain 59 ml DMEM and 59 ml F12. Accordingly, when using this method of making a culture medium, the final concentrations (v/v) mit 500 ml total volume are as follows:
  DMEM: 250 ml+59 ml=309 ml, corresponds to 309/500=61.8% (v/v)
  M171: 118 ml, corresponds to 118/500=23.6% (v/v)
  F12: 59 ml, corresponds to 59/500=11.8% (v/v).

Embodiments of this method of making a culture medium further comprise adding v. 1 ml EGF stock solution (5 µg/ml) to achieve a final EGF concentration of 10 ng/ml, and vi. Insulin 0.175 ml stock solution (14.28 mg/ml) to achieve a final insulin concentration of 5 µg/ml.

It is noted here that in these embodiments, the above-mentioned volumes of these components i. to vi when result in a final volume of 499.675 ml culture medium. If no further components are added to the culture medium, the remaining 0.325 ml (to add up to a volume of 500 ml) can, for example, be any of components i. to iv, that means either DMEM, M171, DMEM/F12 or FBS. Alternatively, the concentration of the stock solution of EGF or Insulin can of course be adjusted such that the total volume of the culture medium is 500 ml. In addition, it is also noted that components i. to iv. do not necessarily have to be added in the order in which they are listed but it is of course also possible to use any order to mix these components to arrive at the culture medium of the present invention. This means, that for example, M171 and DMEM/F12 can be mixed together and then combined with DMEM and FBS to reach final concentrations as described here, i.e. a final concentration of DMEM of about 55 to 65% (v/v), a final concentration of F12 of about 5 to 15% (v/v), a final concentration of M171 of about 15 to 30% (v/v) and a final concentration of FBS of about 1 to 8% (v/v).

In other embodiments, the method further comprises adding to DMEM a volume of 0.325 ml of one or more of the following supplements: adenine, hydrocortisone, 3,3',5-Triiodo-L-thyronine sodium salt (T3), thereby reaching a total volume of 500 ml culture medium. In this embodiments, the final concentration of these supplements in DMEM may be as follows:
  about 0.05 to 0.1 µg/ml adenine, for example about 0.025 µg/ml adenine,
  about 1 to 10 µg/ml hydrocortisone,
  about 0.5 to 5 ng/ml 3,3',5-Triiodo-L-thyronine sodium salt (T3), for example 1.36 ng/ml 3,3',5-Triiodo-L-thyronine sodium salt (T3).

In line with the above disclosure, the invention is also directed to a cell culture medium that is obtainable or that is obtained by the method of making the medium as described here.

In addition, the invention also concerns a method of isolating mesenchymal stem cells from the amniotic membrane of the umbilical cord, wherein this method comprises cultivating amniotic membrane tissue in the culture medium prepared by the method as described here.

Thus, the present invention is also directed to a cell culture medium comprising:
  DMEM in the final concentration of about 55 to 65% (v/v),
  F12 in a final concentration of about 5 to 15% (v/v),
  M171 in a final concentration of about 15 to 30% (v/v) and
  FBS in a final concentration of about 1 to 8% (v/v).

In certain embodiments of the culture medium described here, the medium comprises DMEM in the final concentration of about 57.5 to 62.5% (v/v), F12 in a final concentration of about 7.5 to 12.5% (v/v), M171 in a final concentration of about 17.5 to 25.0% (v/v) and FBS in a final concentration of about 1.75 to 3.5% (v/v). In other embodiments the culture medium may comprise DMEM in a final concentration of about 61.8% (v/v), F12 in a final concentration of about 11.8% (v/v), M171 in a final concentration of about 23.6% (v/v) and FBS in a final concentration of about 2.5% (v/v).

In addition, the culture medium may further comprise Epidermal Growth Factor (EGF) in a final concentration of about 1 ng/ml to about 20 ng/ml. In certain embodiments, the culture medium comprise EGF in a final concentration of about 10 ng/ml. The culture medium described herein may further comprise Insulin in a final concentration of about 1

µg/ml to 10 µg/ml. In such embodiments the culture medium may comprise Insulin in a final concentration of about 5 µg/ml.

The cell culture medium of the invention may further comprise at least one of the following supplements: adenine, hydrocortisone, and 3,3',5-Triiodo-L-thyronine sodium salt (T3). In certain embodiments the culture medium comprises all three of adenine, hydrocortisone, and 3,3',5-Triiodo-L-thyronine sodium salt (T3). If present, the culture medium may comprise adenine in a final concentration of about 0.01 to about 0.1 µg/ml adenine or of about 0.05 to about 0.1 µg/ml adenine, hydrocortisone in a final concentration of about 0.1 to about 10 µg/ml hydrocortisone or of about 1 to about 10 µg/ml hydrocortisone and/or 3,3',5-Triiodo-L-thyronine sodium salt (T3) in a final concentration of about 0.5 to about 5 ng/ml.

In embodiments of the cell culture medium, 500 ml of the cell culture medium of the present invention comprise:
i. 250 ml of DMEM
ii. 118 ml M171
iii. 118 ml DMEM/F12
iv. 12.5 ml Fetal Bovine Serum (FBS) (final concentration of 2.5%)

In further embodiments, the cell culture medium may further comprise
v. EGF in a final concentration of 10 ng/ml, and
vi. Insulin in a final concentration of 5 µg/ml.

Both, insulin and and EGF can be added to to the culture medium using a stock solution of choice, such that the total volume of the culture medium does not exceed 500 ml.

In a particular example, the components i. to vi. of the culture medium of the present invention are the components indicated in FIG. 1, meaning they are obtained from the respective manufacturers using the catalogue number indicated in FIG. 1. The medium that is obtained from mixing the components i. to vi. as indicated in FIG. 1 is also referred herein as "PTT-6". It is again noted in this context that the constituents i. to vi. as well as any other ingredient such as an antibiotic of any other commercial supplier can be used in making the medium of the present invention.

In addition, the cell culture medium of the invention may comprise adenine in a final concentration of about 0.01 to about 0.1 µg/ml adenine or of about 0.05 to about 0.1 µg/ml adenine, hydrocortisone in a final concentration of about 0.1 to 10 µg/ml, of about 0.5 to about 10 µg/ml, or of about 1 to about 10 µg/ml hydrocortisone and/or 3,3',5-Triiodo-L-thyronine sodium salt (T3) in a final concentration of about 0.1 to about 5 ng/ml or of about 0.5 to about 5 ng/ml.

Finally, the invention also provides a method of treating a patient having a disease, the method comprising administering to the patient a mesenchymal cord lining stem cell or a pharmaceutical composition containing a stem cell as disclosed herein. The disease can be any disease that described above. For treating the subject, the mesenchymal stem cell population of the invention may be administered in any suitable way, for example, including but not limited to, topical administration, by implantation or by injection. The stem cell population may, for example, be placed directly onto a wound such as a burn or a diabetic wound (see International patent application WO2007/046775). Alternatively, the stem cell population may also be implanted subcutaneously, for example, directly under the skin, in body fat or the peritoneum.

The invention will be further illustrated by the following non-limiting Experimental Examples.

Experimental Examples

1. Cryopreservation of Umbilical Cord Tissue Prior to Isolation of Mesenchymal Stem Cells Umbilical cord tissue (the umbilical cords were donated with informed consent of the mother) was processed for the subsequent isolation of the mesenchymal stem cells from the amniotic membrane of the umbilical cord as follows.

1.1 Washing of Umbilical Cord Tissue Sample a. Remove scalpels from the protective cover.
b. Hold the umbilical cord securely using the forceps and cut the cord into a 10 cm length piece using a scalpel. Place the unusable cord back in the original tissue cup.
c. Transfer the 10 cm long umbilical cord piece into a new 150 mm culture dish. The 150 mm culture dish may be used in place of the cups.
d. Use the cover of the 150 mm culture dish as a resting place for forceps and scalpel.
e. Remove 25 ml Plasmalyte A (Baxter, Catalog #2B2543Q) with a 30 ml syringe. Hold the syringe at a 45° angle using one hand and dispense the Plasmalyte A directly onto the umbilical cord tissue.
f. Holding the culture dish at a slight angle remove the Plasmalyte A with a 30 ml syringe and blunt needle.
g. Collect used Plasmalyte A in a 300 ml transfer bag that serves as a trash container and dispose it in the biohazard bin.
h. Repeat wash procedure, if necessary using a new culture dish for each wash. Make sure all blood clots on the surface have been removed. More Plasmalyte A can be used if needed to clean the tissue.
i. Place the tissue into a new labeled tissue culture dish to continue cutting the tissue. Place 20 ml of Plasmalyte A into the dish so the tissue does not dry out while cutting it.
j. Cut the cords into equal approximately 1-cm sections resulting in 10 sections in total.
k. Further cut each 1 cm section into smaller pieces with approximately 0.3 cm×0.3 cm to 0.5 cm×0.5 cm per section.
l. Remove any Plasmalyte A that is in the dish.
m. Pull 25 ml Plasmalyte A with a 30 ml syringe from the original Plasmalyte A bag and dispense directly on the umbilical cord tissue pieces.
n. Hold culture dish in an angle to collect all Plasmalyte A used for washing the tissue on one side and remove it with a syringe and blunt needle.
o. Repeat wash one more time. There should not be any clots left.

NOTE: If the cord is not frozen right away, the umbilical cord tissue is kept in Plasmalyte A until ready to freeze.

1.2 Cryopreservation of Umbilical Cord Tissue a. Prepare cryopreservation solution:
  i. Prepare 50 ml freezing solution consisting of 60% Plasmalyte A, 30% of 5% Human Serum Albumin, and 10% dimethyl sulfoxide (DMSO).
  ii. Label a 150 ml transfer bag with "Tissue freeze solution" and attach a plasma transfer set to the port using aseptic technique.
  iii. Remove 30 ml Plasmalyte A with a 30 ml Syringe from the original Plasmalyte A bag and transfer it in the transfer bag labeled "tissue freeze solution" with the time and date solution is made.
  iv. Remove 15 ml of 5% Human Serum Albumin with a 20 ml syringe and transfer it into the labeled transfer bag.
  v. Add 5 ml DMSO to the transfer bag.
  vi. Mix well and record mixing of freeze solution
b. Remove the Plasmalyte A from the tissue before adding the freeze solution.
c. Using a 60 ml syringe, pull all 50 mls of the freeze solution into the syringe add approximately 30 ml freeze solution to the 150 mm cell culture dish containing the umbilical cord tissue. Place a blunt needle on the syringe to keep it sterile.
d. Swirl the culture dish containing the tissue and freezing solution every minute for 10 minutes.
e. Using forceps, select 8 randomly chosen sections and place them in each of the four 4 ml cryovials. Select 4 randomly chosen sections and place them into one 1.8 ml cryovial. These sections should be free of blood clots.
f. Fill each cryovial containing the umbilical cord tissue with the remaining freezing solution to the 3.6 ml filling line for the 4 ml tubes and the 1.8 ml line for the 1.8 ml Nunc vial.
g. Label one Bactec Lytic/10—Anaerobic/F and one Bactec Plus Aerobic/F bottle with tissue ID.
h. Remove 20 ml freeze solution from the culture dish with a syringe and a blunt needle, after wiping the Bactec vials with an alcohol swab, switch the blunt needle for an 18 g needle and inoculate the aerobic and the anaerobic Bactec bottles with 10 ml each.
i. Start controlled rate freezer.
j. After controlled rate freeze is completed place the units in a continuous temperature monitored liquid nitrogen freezer until further use.

2. Isolation of Mesenchymal Cord Lining Stem Cells from Umbilical Cord Tissue

2.1 Preparing Media for Processing MSCs from Umbilical Cord Tissue a. To make 500 ml PTT6 (culture/growth media) add the following in the order listed:
  i. DMEM, 250 ml
  ii. M171 118 ml
  iii. DMEM F12 118 ml
  iv. FBS 12.5 ml (final concentration of 2.5%)
  v. EGF 1 ml (final concentration of 10 ng/ml)
  vi. Insulin 0.175 ml (final concentration of 5 µg/ml)
The above-mentioned volumes of components i. to vi when result in a final volume of 499.675 ml culture medium. If no further components are added to the culture medium, the remaining 0.325 ml (to add up to a volume of 500 ml) can, for example, be any of components i. to iv, that means either DMEM, M171, DMEM/F12 or FBS. Alternatively, the concentration of the stock solution of EGF or Insulin can of course be adjusted such that the total volume of the culture medium is 500 ml. Alternatively, a stock solution of an antibiotic such as Penicillin-Streptomycin-Amphotericin can be added to result in a final volume of 500 ml. It is also possible to add to the culture medium a volume of 0.325 ml of one or more of the following supplements: adenine, hydrocortisone, 3,3',5-Triiodo-L-thyronine sodium salt (T3), thereby reaching a total volume of 500 ml culture medium.

vii. Label the bottle "PTT6" with date media was prepared, initial of the operator, and the phrase "expires on" followed by the expiration date. Expiration date is the earliest expiration date of any of the component or 1 month from the preparation date, whichever comes first.
b. To make the rinse media (Hank's Buffered Salt Solution (HBSS) without Calcium or Magnesium and with 5% FBS), add 2.5 ml FBS to 47.5 ml of HBSS in a 50 ml centrifuge tube. Label the tube "Rinse Media" with operator initials and date the media is made.
c. All media will be tested for sterility using Bactec Lytic/10— Anaerobic/F (Becton Dickinson & Company) and Bactec Pluc+Aerobic/F (Becton Dickinson & Company). Inject 20 ml of prepared media into each bottle.

2.2 Thawing of Umbilical Cord Tissue for MSC Harvesting a. Initiate the thaw once an operator is prepared to process the sample in the clean room. Do not thaw more than 1 vial at a time unless the vials originate from the same donor.
b. Wipe the water bath with disinfectant followed by 70% isopropanol and fill it with 1 L sterile water. Heat the water bath up to 36-38° C.
c. Prepare 10 mL of rinse medium consisting of 70% to 90% PlasmaLyte A in the clean room under a biosafety cabinet. Sterile filter the solution with a 0.2-µm syringe filter attached to a 10 ml syringe and keep the solution refrigerated until use.
d. Place a processing label on a 50 ml conical tube.
e. Confirm water bath temperature is at 36-38° C.
f. Take vial(s) of tissue from the liquid nitrogen storage and thaw rapidly in the 37° C. water bath filled with 1 L of sterile water. The vial holder for the Mr. Frosty Nalgene Cryo 1° C. freezing container floats with vials in place and can be used as a floating rack when thawing samples.
g. Remove the vial from the water bath and spray them with 70% Isopropanol solution. A good time to pull the vial from the water bath is when small ice can be seen floating in the vial—suggest internal temperature of the vial is less than 37° C.
h. Place vial into pass-through and alert the clean room processing technician.

2.3 Preparing for Tissue Processing a. Umbilical cord tissue processing should be performed in an environmentally monitored (EM) clean room. At the end of each shift, full room and hood cleaning are performed
b. Prepare/clean the biosafety cabinet.
c. Perform viable particle counting while working in the biosafety cabinet.
d. Assemble all necessary supplies in the biosafety cabinet checking each for packaging damage and expiration dates. When handling syringes, serological pipets, sterile forceps, scalpels, tissue plates, and needles, make sure not to touch any surface that will come in contact with the sterile product. Only the exterior of the syringe barrel, tubing, plunger tip and/or needle cap or sheath may be safely handled. Discard supply if the surface has been touched or has touched a non-sterile surface.

e. Record lot numbers and expiration dates (if applicable) of all reagents and supplies to be used.
f. Receive the thawed vial by cleaning the vial with lint-free wipe moistened with 70% alcohol before transferring into the biosafety cabinet.
g. Using an aspirating needle with a syringe, withdraw as much liquid from the vial. Avoid suctioning the tissue.
h. Using sterile forceps, transfer the tissue into a sterile 100 mm petri dish.
i. Add an aliquot of 5 ml rinse medium to the tissue fragments.
j. Swirl the contents for 15-30 seconds, then remove the rinse medium with a pipette or syringe with aspirating needle. Repeat this rinse process twice.
k. Add 2 mL of rinse medium to the tissue to avoid drying out the tissue.

2.4. Initiating MSC Outgrowth from Tissue a. Label the bottom of a 6-well plate "Outgrowth 1" with MSC lot number or umbilical cord tissue ID and the date outgrowth is initiated. If 60 mm tissue culture dish is used, divide the plate into 4 quadrants by drawing a grid on the bottom of the dish.
b. Using sterile, disposable forceps, place one 3×3 mm to 5×5 mm tissue into each well. If using a 60 mm tissue culture dish, place the tissue into the middle of each quadrant to keep the tissues apart (more than 1 cm from each other).
c. Fill each well with 3 ml of PTT6.
d. Using an aspirating needle coupled to 30 ml syringe, withdraw enough media to barely cover the tissue. Do not tilt the plate. Do not touch the bottom of the well with the aspirating needle.
e. Using an inverted light microscope, observe for cell outgrowth every day (24±6 hrs). Real time cell culture imaging system may be used in place of the light microscope.
f. Change media every day. Be sure to equilibrate the media to room temperature before use.
  i. Aspirate off the medium.
  ii. Add 3 ml of PTT6.
  iii. Aspirate until tissue is barely submerged in the medium.
g. When cellular outgrowth is observed from the tissue, transplant the tissue to a new 6-well plate using the same procedure as 4.a to 4.e above except label the plate "Outgrowth 2". Maintain cell outgrowth in "Outgrowth 1" plate by adding 2 ml of PTT6 to each well. Observe for confluency every day. Replace media every 2-3 days (be sure to equilibrate the media to room temperature before use).
h. When cell outgrowth is observed in "Outgrowth 2" plate, repeat step 4.a to 4.e except label the plate "Outgrowth 3." Maintain cell outgrowth in "Outgrowth 2" plate by adding 2 ml of PTT6 to each well. Observe for confluency every day. Replace media every 2-3 days (be sure to equilibrate the media to room temperature before use).
i. When outgrowth is observed in "Outgrowth 3" plate, discard the tissue. If the tissues are very small and do not seem to interfere with cell growth, dispose of the tissue when subculturing.
j. When cells reach 40-50% confluency, observe cells every days to prevent over-expansion.
k. When cells reach 70-80% confluency, subculture the cells. Do not allow cells to expand beyond 80% confluence.

With the size of the tissue explants being about 1-3 mm, and the tissue explant/cell culture is performed in 175 mm squared culture dishes, the average number of mesenchymal stem cells harvested from an explant is typically about 4,000-6,000 cells/explant. Accordingly, when the mesenchymal stem cells are simultaneously grown out of 48 explants about 300,000 cells can be obtained at harvest. These 300,000 mesenchymal stem cells collected from explants can then be used for subculturing by seeding a 175 cm 2 cell culture flask with such 300,000 cells as described in the following Example 2.5 (this can be referred to as Passage 1). The mesenchymal stem cells obtained from this passage 1 can then be used to seed again 175 cm 2 flasks (Passage 2) and expand the cells as described in the following Example 2.5. The cells obtained from both Passage 1 and Passage 2 can be "banked" by cryo-preservation, with the mesenchymal stem cells obtained after Passage 2 being considered to represent the Master Cell Bank which will be for further expansion of the mesenchymal stem cells, for example, in a bioreactor as explained below in Example 2.7.

2.5. Subculturing MSC in Cell Culture Dishes a. Perform viable particle while working in the biosafety cabinet. Equilibrate all media to room temperature before use.
b. When cell outgrowth reaches about 70-80% confluency, subculture cells.
  i. Remove PTT6 from the petri dish.
  ii. Rinse with HBSS without Calcium or Magnesium.
  iii. Add 0.2 ml 1× TrypLE-EDTA and swirl for 1-2 minutes. iv. Tilt the dish 30-45° to allow cells to shift down by gravitational flow. Gentle tapping on the side of the plate expedites detachment.
  v. Add 1 ml of PTT6. Pipette up and down gently then transfer cells to a 15 ml centrifuge tube. Use clean pipette tip with each well. Cells from all 6 wells can be pooled into a single 15 ml tube.
  vi. Centrifuge for 10 minutes at 1200 rpm.
  vii. Remove supernatant and resuspend cells with 5 ml PTT6.
c. Subculturing MSC
  i. Aliquot 50 µl of the cell suspension and assay for TNC and viability by Trypan Blue Exclusion Assay.
  ii. Count cells using a hemocytometer. Expect to count 20-100 cells/square. If the count higher than 100, dilute the original sample 1:5 and repeat Trypan Blue method using a hemocytometer.
  iii. Calculate viable cells/ml and total viable cells:
    1. Viable cells/ml=viable cell count×dilution factor×$10^4$
    2. Total viable cells=viable cell count×dilution factor×total volume×$10^4$
  iv. Calculate % viability:
    1. % viability=viable cell count×100/(viable cell count+dead cell count)
  v. Dilute the cell suspension to $1.0×10^6$ cells/ml:
    1. "X" volume=Total viable cells/$10^6$ cells/ml
    2. For example, if total viable cell number is $1.0×10^7$;
    3. "X"=$10^7/10^6$ cells/ml or 10 ml, therefore, you would bring your total cell volume up to 10 ml by adding 5 ml to your cell suspension (that is at 5 ml).

vi. If the cell suspension is less than 106/ml, determine the volume required to seed $2\times10^6$ cells for each 150 mm petri dish or 175 cm$^2$ flask.
   1. Volume for $2\times10^6$ cells=$2\times10^6$ cells÷ viable cells/ml
   2. For example, if viable cells/ml is 8×10 5 cells/ml, $2\times10^6$ cells÷ $8\times10^5$ cells/ml or 2.5 ml are needed.
vii. Set aside 0.5 ml for MSC marker analysis.
viii. Seed $2\times10^6$ cells to each 150 mm petri dish or 175 cm 2 flask with 30 ml PTT6.
ix. Observe cells for attachment, colony formation, and confluence every three days. When cells reach 40-50% confluence, observe cells every one-two days to prevent over-expansion. DO NOT allow cells to expand beyond 80% confluence. A real time cell culturing monitoring system can be used in place of the light microscope.
x. Replace media every 2-3 days.

2.6 Cryopreserving MSC Cells a. Perform viable particle while working in the biosafety cabinet.
b. When cells reach 70-80% confluence, detach cells using 2 ml 1× TrypLE-EDTA for each 150 mm petri dish or 175 cm$^2$ flask.
   i. Remove PTT6 from the petri dish.
   ii. Wash with 5 ml HBSS or PBS without calcium or magnesium.
   iii. Add 2 ml 1× TrypLE-EDTA and swirl for 1-2 minutes.
   iv. Tilt the dish 30-45° to allow cells to shift down by gravitational flow. Gentle tapping on the side of the petri dish helps to expedite detachment.
   v. Add 10 ml PTT6 to inactivate TrypLE. Mix well to dissociate cell clumps.
   vi. Transfer cells to 15 ml centrifuge tube using a Pasteur pipette.
   vii. Centrifuge for 10 minutes at 1200 rpm.
   viii. Aspirate medium and resuspend with 10 ml PTT6.
   ix. Aliquot 50 µl and determine total viable cell number and % viability as above. Cell count will need to be performed within 15 minutes as the cells may start clumping.
c. Preparing cells for cryopreservation
   i. Prepare Cell Suspension Media and Cryopreservation Media and freeze the cells

2.7. Subculturing (Expansion) of MSC in a Quantum Bioreactor (Terumo BTC, Inc It is also possible to use a Quantum Bioreactor can used to expand the MSC. The starting cell number for the expansion in the Quantum Bioreactor should range between 20 to 30 million cells per run. The typical yield per run is 300 to 700 million MSC at harvest. The Bioreactor is operated following the protocol of the manufacturer. The so obtained mesenchymal stem cells are typically cryo-preserved (see below) and serve as Working Cell Bank.

Materials/Reagents:
1. Quantum Expansion Set
2. Quantum Waste Bag
3. Quantum Media Bag
4. Quantum Inlet Bag
5. PTT6
6. PBS
7. Fibronectin
8. TrypLE
9. 3 ml syringe
10. Glucose test strips
11. Lactate test strips
12. 60 ml Cell Culture Plate or equivalent
13. Medical Grade 5% $CO_2$ Gas-mix
14. 50 ml Combi-tip Equipment:
1. Biosafety Cabinet
2. Glucose Meter (Bayer Healthcare/Ascensia Contour Blood Glucose Meter)
3. Lactate Plus (Nova Biomedical)
4. Peristaltic pump with head
5. Centrifuge, Eppendorf 5810
6. Sterile Tube Connector
7. M4 Repeat Pipettor
8. RF Sealer Procedure:
1. Preparing the Quantum Bioreactor
   a) Priming the Quantum Bioreactor
   b) Coating the bioreactor:
      1) Prepare the fibronectin solution in the biosafety cabinet.
         1) Allow lyophilized fibronectin to acclimate to room temperature (>15 min at room temperature)
         2) Add 5 ml of sterile distilled water; do not swirl or agitate
         3) Allow fibronectin to go into solution for 30 min.
         4) Using a 10 ml syringe attached with an 18 g needle, transfer the fibronectin solution to a Ccell inlet bag containing 95 ml of PBS.
      2) Attach the bag to the "reagent" line
      3) Check for bubbles (bubbles may be removed by using "Remove IC Air" or "Remove EC Air" and using "Wash" as the inlet source.
      4) Open or set up program for coating the bioreactor
      5) Run the program
      6) While the program is running to coat the bioreactor, prepare a media bag with 4 L of PTT6 media.
      7) Attach the media bag to the IC Media line using a sterile tube connector.
      8) When the bioreactor coating steps are completed, detach the cell inlet bag used for fibronectin solution using a RF sealer.
   c) Washing off excess fibronectin
   d) Conditioning the bioreactor with media
2. Culturing the Cells in the Quantum Bioreactor
   a) Loading and attaching the cells with Uniform Suspension:
   b) Feeding and cultivation of the cells
      1) Chose media flow rate to feed the cells.
      2) Sample for lactate and glucose everyday.
      3) Adjust the flow rate of the media as the lactate levels increase. The actual maximal tolerable lactate concentration will be defined by a flask culture from which the cells originate. Determine if adequate PTT6 media is in the media bag. If necessary, replace the PTT6 media bag with a fresh PTT6 media bag.
      4) When the flow rate has reached the desired value, measure lactate level every 8-12 hours. If the lactate level does not decrease or if the lactate level continues to increase, harvest the cells.
3. Harvesting the Cells from the Quantum Bioreactor
   a) When lactate concentration does not decrease, harvest the cells after sampling for lactate and glucose for the last time.

b) Harvesting the cells:
1) Attach cell inlet bag filled with 100 ml TrypLE to the "Reagent" line using a sterile tube connector.
2) Confirm sufficient PBS is in the PBS bag. If not, attach a new bag with at least 1.7 liters of PBS to the "Wash" line using a sterile tube connector.
3) Run the Harvest program 4. Cryopreserving the Cells
1) Once the cells have been harvested, transfer the cells to 50 ml centrifuge tube to pellet the cells.
2) Resuspend using 25 ml of cold cell suspension solution. Count the cells using Sysmex or Biorad Cell counter. Attach the cell count report to the respective Quantum Processing Batch Record.
3) Adjust cell concentration to $2 \times 10^7$/ml
4) Add equal volume cryopreservation solution and mix well (do not shake or vortex)
5) Using a repeat pipettor, add 1 ml of the cell suspension in cryopreservative to each 1.8 ml vial. Cryopreserve using the CRF program as described in the SOP D6.100 CB Cryopreservation Using Controlled Rate Freezers
6) Store the vials in a designated liquid nitrogen storage space.
7) Attach the CRF run report to the form respective MSC P3-Quantum Processing Batch Record.

3. Analyis of Stem Cell Marker Expression in Mesenchymal Cord Lining Stem Populations Isolated from Umbilical Cord Tissue, Using Different Culture Media Flow cytometry experiments were carried out to to analyse mesenchymal stem cells isolated from the umbilical cord for the expression of the mesenchymal stem cell markers CD73, CD90 and CD105.

For these experiments, mesenchymal stem cells were isolated from umbilical cord tissue by cultivation of the umbilical cord tissue in three different cultivation media, followed by subculturing of the mesenchymal stem cells in the respective medium as set forth in Example 2.

The three following culture media were used in these experiments: a) 90% (v/v/DMEM supplemented with 10% FBS (v/v), b) the culture medium PTT-4 described in US patent application 2006/0078993 and the corresponding International patent application WO2006/019357 that consist of 90% (v/v) CMRL1066, and 10% (v/v) FBS (see paragraph of WO2006/019357 and c) the culture medium of the present invention PPT-6 the composition of which is described herein. In this flow cytometry analysis, two different samples of the cord lining mesenchymal stem cell (CLMC) population were analysed for each of the three used culture media.

The following protocol was used for the flow cytometry analysis.

Materials and Methods

| Instruments name | Company Name | Serial Name |
| --- | --- | --- |
| BD FACS CANDO | BD | V07300367 |
| Inverted Microscope, CKX41SF | Olympus | 4K40846 |
| Centrifuge, Micro spin Tabletop | Biosan | 010213-1201-0003 |

| Reagent list | Company Name | CatLog Number |
| --- | --- | --- |
| 10 X Trypsin | Biowest | X0930-100 |
| 10 X PBS | Lonza | 17-517Q |
| DMEM | Lonza | 12-604F |
| Fetal Bovine Serum | GE healthcare | A11-151 |

| Antibody list | Company Name | CatLog Number |
| --- | --- | --- |
| Human CD73 Purified AD2 0.1 mg | BD | 550256 |
| Human CD90 Purified 5E10 1 mL | BD | 550402 |
| Human CD105 Purified 266 0.1 mg | BD | 555690 |
| Alexa Fluor 647 goat anti-mouse IgG (H + L) *2 mg/mL* | BD | A21235 |

| Reagents name | Composition |
| --- | --- |
| 1 X PBS (1L) | 100 ml of 10 X PBS + 900 ml of sterile distilled H20 |
| 1x PBA (50 ml) | 49.5 ml of 1XPBS + 0.5 ml of FBS |

Procedure a) Cell Isolation and Cultivation from the Umbilical Cord Lining Membrane
1. Explant tissue samples were incubated in a cell culture plate and submerged in the respective medium, then keep it in $CO_2$ incubator at 37° C. as explained in Example 2.
2. The medium was changed every 3 days.
3. Cell outgrowth from tissue culture explants was monitored under light microscopy.
4. At a confluence of about 70%, cells were separated from dish by trypsinization (0.0125% trypsin/0.05% EDTA) and used for flow cytometry experiments.

b) Trypsinization of Cells for Experiments
1. Remove medium from cell culture plate
2. Gently rinse with sterile 1×PBS to remove traces of FBS as FBS will interfere with the enzymatic action of trypsin.
3. Add 1× trypsin to cell culture plate and incubate for 3-5 min in 37° C.
4. Observe cells under microscope to ensure that they are dislodged. Neutralize trypsin by adding complete media containing FBS (DMEM with 10% FBS).
5. Use a pipette to break up cell clumps by pipetting cells in media against a wall of the plate. Collect and transfer cell suspension into 50 ml centrifuge tubes
6. Add sterile 1×PBS to plate and rinse it, Collect cell suspension into the same centrifuge tube.
7. Centrifuge it at 1800 rpm for 10 mins.
8. Discard supernatant and re-suspend cell pellet with PBA medium.

c) Counting Cells
1. Ensure that the haemocytometer and its cover slip are clean and dry, preferably by washing them with 70% ethanol and letting them dry before wiping them with Kim wipes (lint-free paper).
2. Aliquot a small amount of cells in suspension into a micro centrifuge tube and remove from the BSC hood.
3. Stain cells in suspension with an equal volume of Trypan Blue, e.g. to 5000 of suspension add 5000 of Trypan Blue (dilution factor=2×, resulting in 0.2% Trypan Blue solution).

4. Avoid exposure of cells to Trypan Blue for longer than 30 mins as Trypan Blue is toxic and will lead to an increase in non-viable cells, giving a false cell count.
5. Add 20 μl of the cell suspension mixture to each chamber of a haemocytometer and view under a light microscope.
   a. Count the number of viable cells (bright cells; non-viable cells take up Trypan Blue readily and thus are dark) in each quadrant of the haemocytometer for a total of 8 quadrants in the upper and lower chamber.
   Total cell count is given as (Average number of cells/quadrant)×$10^4$ cells/ml.

d) Staining Cells
  i. Preparation before staining cells
     Cell suspension are aliquot into 3 tubes (CD73, CD90, CD105) in duplicates and 2 tubes (negative control), each containing 50,000 cells.
  ii. Staining with primary antibody (Ab)
     Add 1 μl [0.5 mg/ml Ab] of primary antibody to 100 ul cell suspension. Incubate at 4° C. for 45 min.
     Make up to 1 ml with PBA.
     Centrifuge 8000 rpm at 4° C. for 5 mins.
     Remove supernatant.
     Add 1 ml of PBA and re-suspend pellet
     Centrifuge 8000 rpm at 4° C. for 5 mins.
     Remove supernatant.
     Re-suspend in 100 ul PBA.
  iii. Staining with secondary Ab—in the dark
     Add 1 ul [0.5 mg/ml ab] of secondary antibody to 100 ul cell suspension. Incubate at 4° C. for 30 min.
     Make up to 1 ml with PBA.
     Centrifuge 8000 rpm at 4° C. for 5 mins.
     Remove supernatant.
     Add 1 ml of PBA and re-suspend pellet
     Centrifuge 8000 rpm at 4° C. for 5 mins.
     Remove supernatant
     Re-suspend in 200-300 ul PBA for flow cytometry analysis
     Transfer cells to FACS tube for reading in BD FACS CANDO flow cytometry.

Figure 2B:
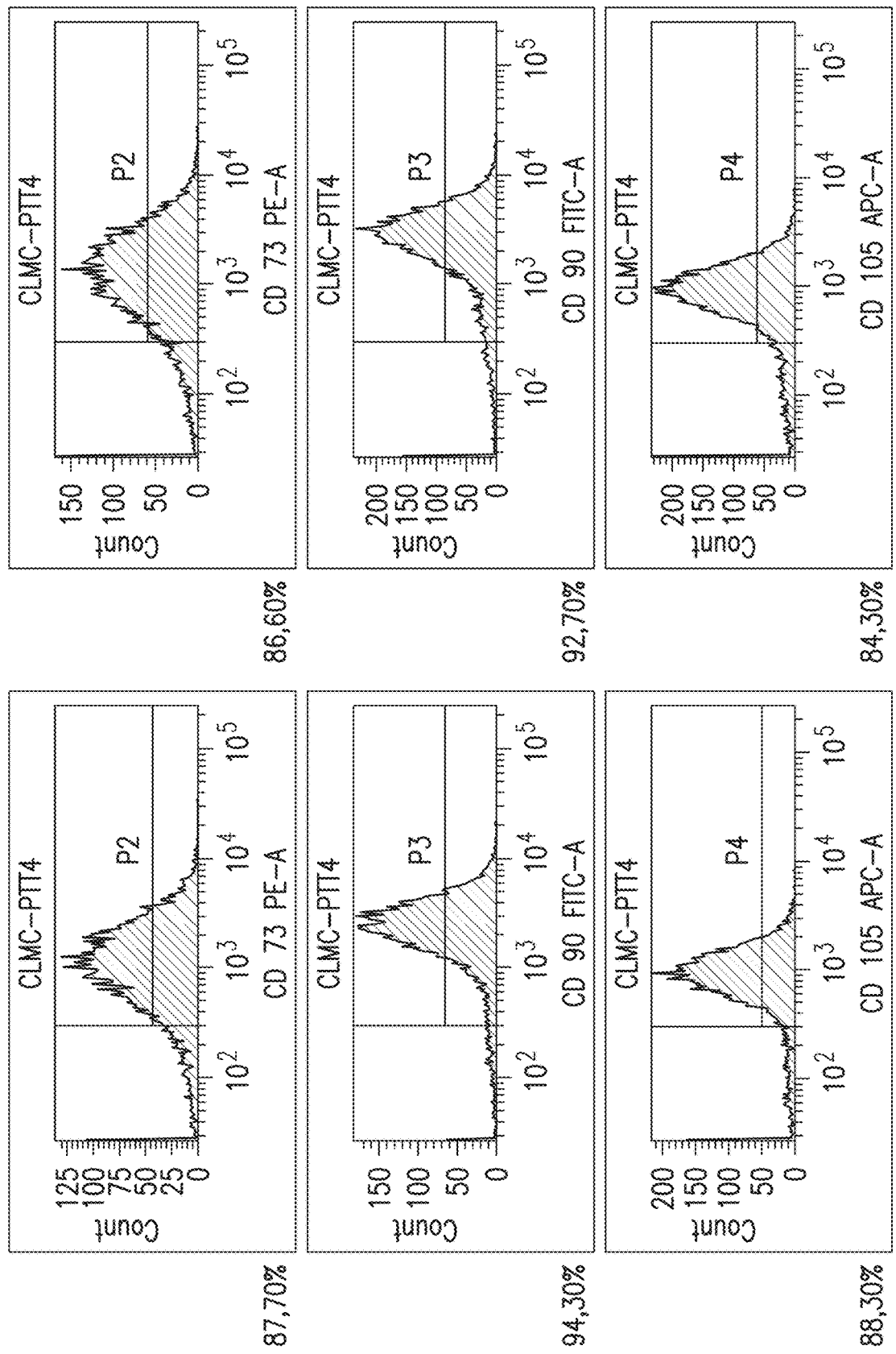
Figure 2C:
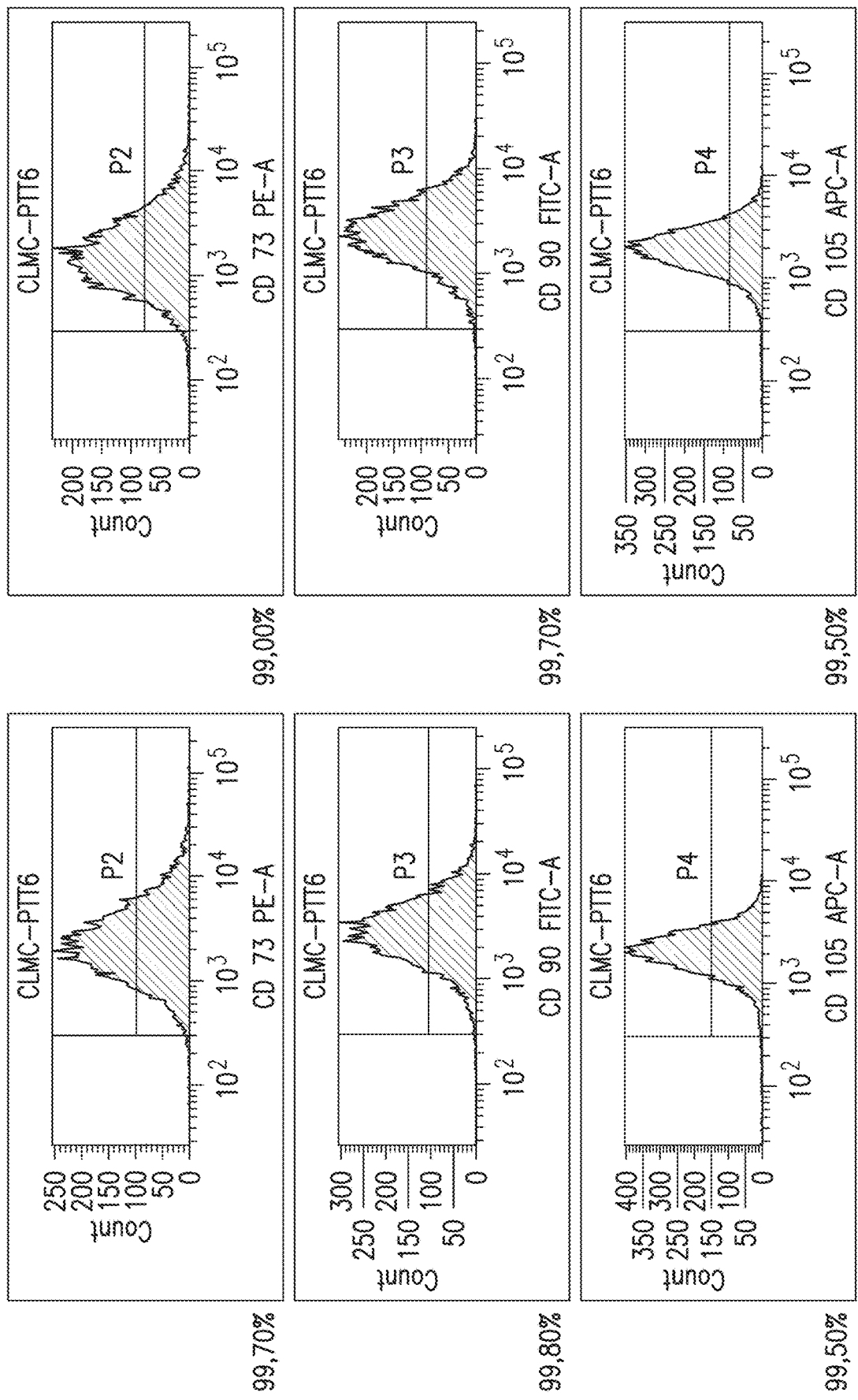

The results of the flow cytometry analysis are shown in FIG. 2a to FIG. 2c. FIG. 2a shows the percentage of isolated mesenchymal cord lining stem cells expressing stem cell markers CD73, CD90 and CD105 after isolation from umbilical cord tissue and cultivation in DMEM/10% FBS, FIG. 2b shows the percentage of isolated mesenchymal cord lining stem cells expressing stem cell markers CD73, CD90 and CD105 after isolation from umbilical cord tissue and cultivation in PTT-4 and FIG. 2c shows the percentage of isolated mesenchymal cord lining stem cells expressing stem cell markers CD73, CD90 and CD105 after isolation from umbilical cord tissue and cultivation in PTT-6. As can be seen from FIG. 2a, the population isolated using DMEM/10% FBS as culture medium cultivation has about 75% CD73+ cells, 78% 90+ cells and 80% CD105+ cells (average of two experiments), while after isolation/cultivation of umbilical cord tissue using PPT-4 culture medium (see FIG. 2b) the number of mesenchymal stem cells that are CD73-positive, CD90-positive and CD105-positive are about 87% (CD73+ cells), 93%/CD90+ cells) and 86% (CD105+ cells) average of two experiments. The purity of the mesenchymal stem cell population that was obtained by means of cultivation in the PTT-6 medium of the present invention is at least 99.0% with respect to all three markers (CD73, CD90, CD105), meaning the purity of this cell population is significant higher than for cultivation using PPT-4 medium or DMEM/10% FBS. In addition and even more importantly, the mesenchymal stem cell population obtained by means of cultivation in PTT-6 is essentially a 100% pure and defined stem cell population. This makes the stem cell population of the present invention the ideal candidate for stem cell based therapies. Thus, this population of mesenchymal cord lining stem cells may become the gold standard for such stem cell based therapeutic approaches.

Figure 3B:
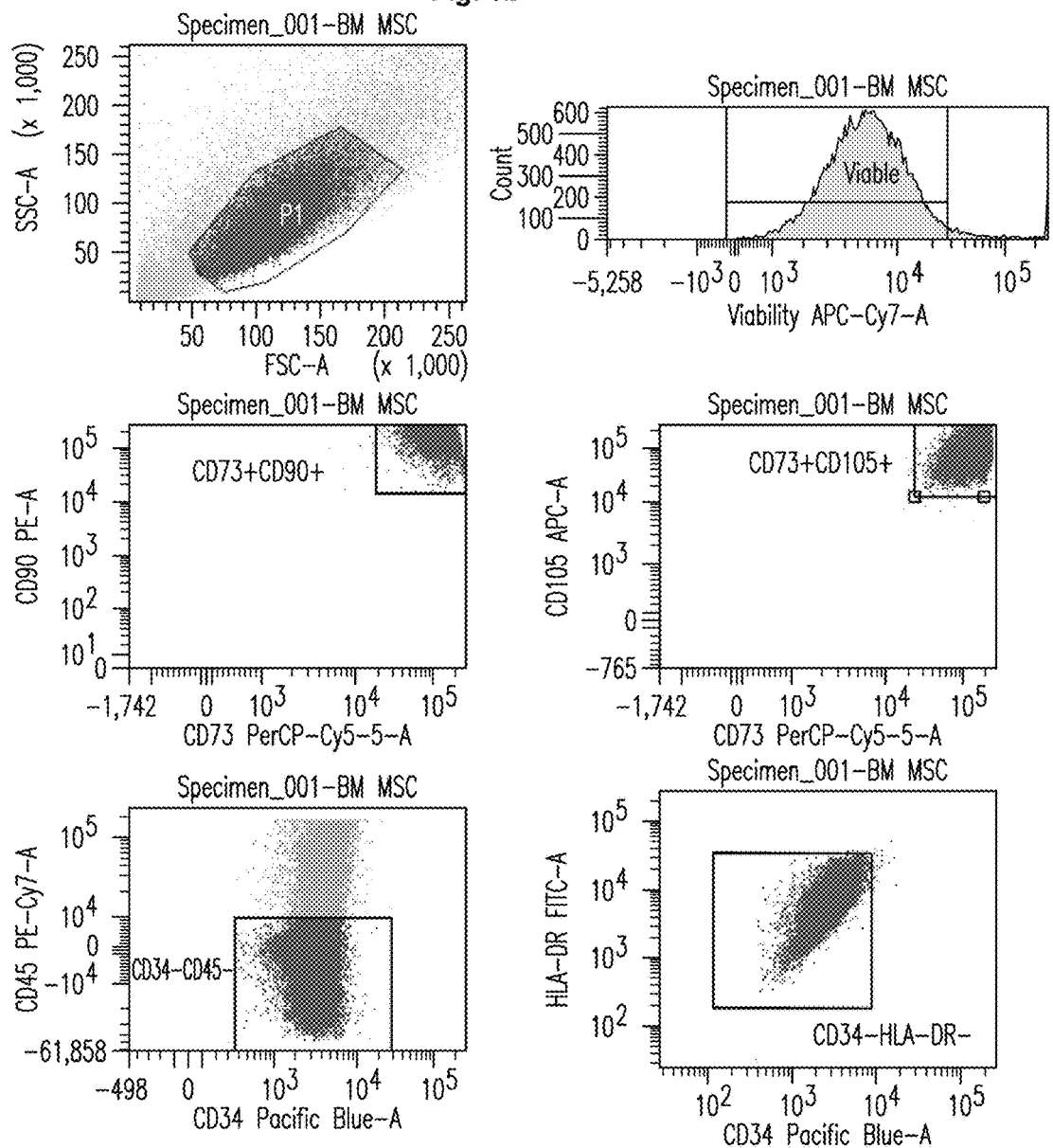

The findings shown in FIGS. 2a-2c are further corroborated by the results of the flow cytometry analysis that are shown in FIG. 3a and FIG. 3b. FIG. 3a shows the percentage of isolated mesenchymal cord lining stem cells (mesenchymal stem cells of the amniotic membrane of umbilical cord) that express the stem cell markers CD73, CD90 and CD105 and lack expression of CD34, CD45 and HLA-DR after isolation from umbilical cord tissue and cultivation in PTT-6 medium. As shown in FIG. 3a, the mesenchymal stem cell population contained 97.5% viable cells of which 100% expressed each of CD73, CD90 and CD105 (see the rows "CD73+CD90+" and "CD73+CD105+") while 99.2% of the stem cell population did not express CD45 and 100% of the stem cell population did not express CD34 and HLA-DR (see the rows "CD34−CD45−" and "CD34−HLA-DR-). Thus, the mesenchymal stem cells population obtained by cultivation in PTT-6 medium is essentially a 100% pure and defined stem cell population that meets the criteria that mesenchymal stem cells are to fulfill to be used for cell therapy (95% or more of the stem cell population express CD73, CD90 and CD105, while 98% or more of the stem cell population lack expression of CD34, CD45 and HLA-DR, see Sensebe et al. "Production of mesenchymal stromal/stem cells according to good manufacturing practices: a review", supra). It is noted here that the present mesenchymal stem cells of the amniotic membrane are adhere to plastic in standard culture conditions and differentiate in vitro into osteoblasts, adipocytes and chondroblasts, see U.S. Pat. Nos. 9,085,755, 8,287,854 or WO2007/046775 and thus meet the criteria generally accepted for use of mesenchymal stem cells in cellular therapy.

FIG. 3b shows the percentage of isolated bone marrow mesenchymal stem cells that express CD73, CD90 and CD105 and lack expression of CD34, CD45 and HLA-DR. As shown in FIG. 3b, the bone marrow mesenchymal stem cell population contained 94.3% viable cells of which 100% expressed each of CD73, CD90 and CD105 (see the rows "CD73+CD90+" and "CD73+CD105+") while only 62.8% of the bone marrow stem cell population lacked expression of CD45 and 99.9% of the stem cell population lacked expression CD34 and HLA-DR (see the rows "CD34−CD45− and "CD34−HLA-DR-). Thus, the bone marrow mesenchymal stem cells that are considered to be gold standard of mesenchymal stem cells are by far less homogenous/pure in terms of stem cell marker than the mesenchymal stem cells population (of the amniotic membrane of the umbilical cord) of the present application. This finding also shows that the stem cell population of the present invention may be the ideal candidate for stem cell based therapies and may become the gold standard for stem cell based therapeutic approaches.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention. The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group. Further embodiments of the invention will become apparent from the following claims.

The invention is further characterized by the following items:

1. A method of isolating a mesenchymal stem cell population from the amniotic membrane of the umbilical cord, the method comprising cultivating umbilical cord tissue in a culture medium comprising DMEM (Dulbecco's modified eagle medium), F12 (Ham's F12 Medium), M171 (Medium 171) and FBS (Fetal Bovine Serum).
2. The method of item 1, wherein the culture medium comprises DMEM in a final concentration of about 55 to 65% (v/v), F12 in a final concentration of about 5 to 15% (v/v), M171 in a final concentration of about 15 to 30% (v/v) and FBS in a final concentration of about 1 to 8% (v/v).
3. The method of item 2, wherein the culture medium comprises DMEM in a final concentration of about 57.5 to 62.5% (v/v), F12 in a final concentration of about 7.5 to 12.5% (v/v), M171 in a final concentration of about 17.5 to 25.0% (v/v) and FBS in a final concentration of about 1.75 to 3.5% (v/v).
4. The method of item 3, wherein the culture medium comprises DMEM in a final concentration of about 61.8% (v/v), F12 in a final concentration of about 11.8% (v/v), M171 in a final concentration of about 23.6% (v/v) and FBS in a final concentration of about 2.5% (v/v).
5. The method of any of items 1 to 4, wherein the culture medium further comprises Epidermal Growth Factor (EGF) in a final concentration of about 1 ng/ml to about 20 ng/ml.
6. The method of any of items 1 to 5, wherein the culture medium comprises EGF in a final concentration of about 10 ng/ml.
7. The method of any of items 1 to 6, wherein the culture medium comprises Insulin in a final concentration of about 1 µg/ml to 10 µg/ml.
8. The method of any of items 1 to 7, wherein the culture medium comprises Insulin in a final concentration of about 5 µg/ml.
9. The method of any of the foregoing items, wherein the culture medium further comprises at least one of the following supplements: adenine, hydrocortisone, and 3,3',5-Triiodo-L-thyronine sodium salt (T3).
10. The method of any of the foregoing items, wherein the culture medium comprises all three of adenine, hydrocortisone, and 3,3',5-Triiodo-L-thyronine sodium salt (T3).
11. The method of item 11 or 12, wherein the culture medium comprises adenine in a final concentration of about 0.01 to about 0.1 µg/ml adenine, hydrocortisone in a final concentration of about 0.1 to about 10 µg/ml hydrocortisone and/or 3,3',5-Triiodo-L-thyronine sodium salt (T3) in a final concentration of about 0.5 to about 5 ng/ml.
12. The method of any of the foregoing items, comprising culturing the umbilical cord tissue till the cell outgrowth of the mesenchymal stem cells of the amniotic membrane reaches about 70-80% confluency.
13. The method of item 12, comprising removing the mesenchymal stem cells from the cultivation container used for the cultivation.
14. The method of item 13, wherein removing the mesenchymal stem cells from the cultivation container is carried out by enzymatic treatment.
15. The method of item 14, wherein the enzymatic treatment comprises trypsination.
16. The method of any of items 13 to 15, wherein the mesenchymal stem cells are transferred for subculturing to a cultivation container for subculturing.
17. The method of item 16, wherein the mesenchymal cells are suspended for subculturing at a concentration $1.0 \times 10^6$ cells/ml.
18. The method of item 17, wherein the mesenchymal stem cells are subcultured in a culture medium as defined in any of the items 1 to 10.
19. The method of item 18, wherein the mesenchymal stem cells are subcultured till the mesenchymal stem cells reach about 70-80% confluency.
20. The method of any of items 16 to 19, wherein the subculturing is carried out in a self-contained bioreactor.
21. The method of item 20, wherein the bioreactor is selected from the group consisting of a parallel-plate bioreactor, a hollow-fiber bioreactor and and a microfluidic bioreactor.
22. The method of any of the foregoing items, wherein the umbilical cord tissue is a piece of the entire umbilical cord or the amniotic membrane of the umbilical cord.
23. The method of any of the foregoing items wherein cultivation is carried out in a $CO_2$ cell culture incubator at a temperature 37° C.
24. The method of item 23, comprising removing the mesenchymal stem cells from the cultivation container used for the subcultivation.
25. The method of item 24, wherein removing the mesenchymal stem cells from the cultivation container is carried out by enzymatic treatment.

26. The method of item 25, wherein the enzymatic treatment comprises trypsination.
27. The method of item 26, further comprising collecting the isolated mesenchymal stem cells.
28. The method of any of the foregoing items, wherein at least about 90% or more, about 91% or more, about 92% or more, about 92% or more, about 93% or more, about 94% or more, about 95% or more, about 96% or more, about 97% or more, about 98% or more about 99% or more of the isolated mesenchymal stem cells express the following markers: CD73, CD90 and CD105.
29. The method of any of the foregoing items, wherein at least about 90% or more, about 91% or more, about 92% or more, about 92% or more, about 93% or more, about 94% or more, about 95% or more, about 96% or more, about 97% or more, about 98% or more about 99% or more of the isolated mesenchymal stem cells lack expression of the following markers: CD34, CD45 and HLA-DR (Human Leukocyte Antigen—antigen D Related).
30. The method of any of items 28 or 29, wherein about 97% or more, about 98% or more about 99% or more of the isolated mesenchymal stem cells express CD73, CD90 and CD105 and lack expression of CD34, CD45 and HLA-DR.
31. The method of any of the foregoing items, further comprising preserving the isolated stem/progenitor cells for further use.
32. The method of item 31, wherein preserving is carried out by cryo-preservation.
33. An isolated mesenchymal stem population of the amniotic membrane of the umbilical cord, wherein at least about 90% or more cells of the stem cell population express each of the following markers: CD73, CD90 and CD105.
34. The mesenchymal stem cell population of item 33, wherein least about 90% or more cells of the stem cell population lack expression of the following markers: CD34, CD45 and HLA-DR.
35. The mesenchymal stem cell population of item 34, wherein at least about 91% or more, about 92% or more, about 92% or more, about 93% or more, about 94% or more, about 95% or more, about 96% or more, about 97% or more, about 98% or more about 99% or more cells of the isolated mesenchymal stem cell population express each of CD73, CD90 and CD105 and lack expression of each of CD34, CD45 and HLA-DR.
36. The mesenchymal stem cell population of any of items 33 to 35, wherein the population is obtainable by the method as defined in any of items 1 to 30.
37. The mesenchymal stem cell population of any of items 33 to 35, wherein the population is obtained by the method as defined in any of items 1 to 30.
38. A pharmaceutical composition comprising an isolated mesenchymal stem population of the amniotic membrane of the umbilical cord, wherein at least about 90% or more cells of the stem cell population express each of the following markers: CD73, CD90 and CD105 and lack expression of each of the following markers: CD34, CD45 and HLA-DR.
39. The pharmaceutical composition of item 38, wherein the pharmaceutical composition is adapted for systemic or topical application.
40. The pharmaceutical composition of item 38 or 39, further comprising a pharmaceutically acceptable excipient.
41. A method of making a culture medium suitable for isolating a mesenchymal stem cell population from the amniotic membrane of the umbilical cord, the method comprising, mixing to obtain a final volume of 500 ml culture medium:
    i. 250 ml of DMEM
    ii. 118 ml M171
    iii. 118 ml DMEM/F12
    iv. 12.5 ml Fetal Bovine Serum (FBS) (final concentration of 2.5%)
42. The method of item 41, further comprising adding
    v. 1 ml EGF stock solution (5 µg/ml) to achieve a final concentration of 10 ng/ml)
    vi. Insulin 0.175 ml stock solution (14.28 mg/ml) to achieve a final concentration of 5 µg/ml.
43. The method of item 41 or 42, further comprising adding to DMEM one or more of the following supplements: adenine, hydrocortisone, 3,3',5-Triiodo-L-thyronine sodium salt (T3), thereby reaching a total volume of 500 ml culture medium.
44. The method of item 43, wherein the final concentration of the supplements in DMEM are as follows.
    about 0.05 to 0.1 µg/ml adenine, for example about 0.025 µg/ml adenine,
    about 1 to 10 µg/ml hydrocortisone,
    about 0.5 to 5 ng/ml 3,3',5-Triiodo-L-thyronine sodium salt (T3), for example 1.36 ng/ml 3,3',5-Triiodo-L-thyronine sodium salt (T3).
45. A cell culture medium obtainable by the method of any of items 41 to 44.
46. A method of isolating mesenchymal stem cells from the amniotic membrane of the umbilical cord, comprising cultivating amniotic membrane tissue in the culture medium prepared by the method as defined in any of items 41 to 44.
47. A cell culture medium comprising:
    DMEM in the final concentration of about 55 to 65% (v/v),
    F12 in a final concentration of about 5 to 15% (v/v),
    M171 in a final concentration of about 15 to 30% (v/v) and
    FBS in a final concentration of about 1 to 8% (v/v).
48. The cell culture medium of item 47, wherein the culture medium comprises DMEM in the final concentration of about 57.5 to 62.5% (v/v), F12 in a final concentration of about 7.5 to 12.5% (v/v), M171 in a final concentration of about 17.5 to 25.0% (v/v) and FBS in a final concentration of about 1.75 to 3.5% (v/v).
49. The cell culture medium of item 48, wherein the culture medium comprises DMEM in a final concentration of about 61.8% (v/v), F12 in a final concentration of about 11.8% (v/v), M171 in a final concentration of about 23.6% (v/v) and FBS in a final concentration of about 2.5% (v/v).
50. The cell culture medium of any of items 47 to 49, wherein the culture medium further comprises Epidermal Growth Factor (EGF) in a final concentration of about 1 ng/ml to about 20 ng/ml.
51. The cell culture medium of any of items 7 to 50, wherein the culture medium comprise EGF in a final concentration of about 10 ng/ml.

52. The cell culture medium of any of items 47 to 51, wherein the culture medium comprises Insulin in a final concentration of about 1 µg/ml to 10 µg/ml.
53. The cell culture medium of item 52, wherein the culture medium comprises Insulin in a final concentration of about 5 µg/ml.
54. The cell culture medium of any of items 47 to 53, wherein the culture medium further comprises at least one of the following supplements: adenine, hydrocortisone, and 3,3',5-Triiodo-L-thyronine sodium salt (T3).
55. The cell culture medium of item 54, wherein the culture medium comprises all three of adenine, hydrocortisone, and 3,3',5-Triiodo-L-thyronine sodium salt (T3).
56. The cell culture medium of item 54 or 55, wherein the culture medium comprises adenine in a final concentration of about 0.05 to about 0.1 µg/ml adenine, hydrocortisone in a final concentration of about 1 to about 10 µg/ml hydrocortisone and/or 3,3',5-Triiodo-L-thyronine sodium salt (T3) in a final concentration of about 0.5 to about 5 ng/ml.
57. The cell culture medium of any of items 47 to 56, wherein 500 ml of the cell culture medium comprise:
  i. 250 ml of DMEM
  ii. 118 ml M171
  iii. 118 ml DMEM/F12
  iv. 12.5 ml Fetal Bovine Serum (FBS) (final concentration of 2.5%)
58. The cell culture medium of item 57, further comprising
  v. EGF in a final concentration of 10 ng/ml
  vi. Insulin in a final concentration of 5 µg/ml.
  vi. Insulin 0.175 ml (final concentration of 5 µg/ml)
59. The cell culture medium of item 57 or 58, further comprising adenine in a final concentration of about 0.05 to about 0.1 µg/ml adenine, hydrocortisone in a final concentration of about 1 to about 10 µg/ml hydrocortisone and/or 3,3',5-Triiodo-L-thyronine sodium salt (T3) in a final concentration of about 0.5 to about 5 ng/ml.
60. The use of a cell culture medium as defined in any of items 47 to 59 for isolation of mesenchymal stem cells from the amniotic membrane of umbilical cord.
61. The use of a cell culture medium as defined in any of items 47 to 59 for cultivation of mesenchymal stem cells from the amniotic membrane of umbilical cord.

What is claimed is:

1. A method of treating a patient in need thereof, comprising: thawing a cryopreserved mesenchymal stem population of the amniotic membrane of the umbilical cord, wherein cells of the stem cell population express the POU5f1 gene, and wherein at least about 97% or more cells of the stem cell population express each of the following markers: CD73, CD90 and CD105 and lack expression of the following markers: CD34, CD45 and HLA-DR; and wherein the cells of the stem cell population are cryopreserved in a freezing solution comprising a cryoprotectant; and
  administering the thawed cryopreserved mesenchymal stem population of the amniotic membrane of the umbilical cord to the patient.
2. The method of claim 1, wherein the disease is a wound.
3. The method of claim 1, wherein the thawed cryopreserved mesenchymal stem population of the amniotic membrane of the umbilical cord is administered to the patient by topical administration, by implantation or by injection.
4. The method of claim 2, wherein the thawed cryopreserved mesenchymal stem population of the amniotic membrane of the umbilical cord is administered to the patient by topical administration, by implantation or by injection.

* * * * *